(12) United States Patent
Iyer et al.

(10) Patent No.: US 9,670,113 B2
(45) Date of Patent: Jun. 6, 2017

(54) NATURAL GAS PROCESSING AND SYSTEMS

(71) Applicant: Siluria Technologies, Inc., San Francisco, CA (US)

(72) Inventors: Rahul Iyer, Kensington, CA (US); Alex Tkachenko, San Francisco, CA (US); Sam Weinberger, San Francisco, CA (US); Erik C. Scher, San Francisco, CA (US); Fabio R. Zurcher, Brisbane, CA (US); Joel M. Cizeron, Redwood City, CA (US); Wayne P. Schammel, San Francisco, CA (US); Joel Gamoras, Vallejo, CA (US); Dmitry Karshtedt, Washington, DC (US); Greg Nyce, Pleasanton, CA (US)

(73) Assignee: Siluria Technologies, Inc., San Francisco, CA (US)

( * ) Notice: Subject to any disclaimer, the term of this patent is extended or adjusted under 35 U.S.C. 154(b) by 350 days.

(21) Appl. No.: 13/936,783

(22) Filed: Jul. 8, 2013

(65) Prior Publication Data
US 2014/0012053 A1    Jan. 9, 2014

Related U.S. Application Data

(60) Provisional application No. 61/773,669, filed on Mar. 6, 2013, provisional application No. 61/669,523, filed on Jul. 9, 2012.

(51) Int. Cl.
  *B01J 8/02*  (2006.01)
  *B01J 8/04*  (2006.01)
  (Continued)

(52) U.S. Cl.
  CPC ........ *C07C 2/82* (2013.01); *B01J 8/02* (2013.01); *B01J 8/04* (2013.01); *C07C 2/06* (2013.01);
  (Continued)

(58) Field of Classification Search
  CPC .................................. C07C 2/82; C07C 2/84
  See application file for complete search history.

(56) References Cited

U.S. PATENT DOCUMENTS 2,486,980 A    11/1949 Robinson
2,579,601 A    12/1951 Nelson et al.
(Continued)

FOREIGN PATENT DOCUMENTS

CA    2765769 A1    1/2011
CN    1403375 A    3/2003
(Continued)

OTHER PUBLICATIONS

Matherne et al. Chapter 14: Direct Conversion of Methane to C2's and Liquid Fuels: Process Economics. Methane Conversion by Oxidative Processes (1992), pp. 463-482.*

(Continued)

*Primary Examiner* — Jennifer A Leung
(74) *Attorney, Agent, or Firm* — Wilson Sonsini Goodrich & Rosati

(57) ABSTRACT

Natural gas and petrochemical processing systems including oxidative coupling of methane reactor systems that integrate process inputs and outputs to cooperatively utilize different inputs and outputs of the various systems in the production of higher hydrocarbons from natural gas and other hydrocarbon feedstocks.

20 Claims, 7 Drawing Sheets

(51) Int. Cl.
  *C07C 2/82* (2006.01)
  *C07C 2/84* (2006.01)
  *C07C 2/06* (2006.01)
  *C10G 50/00* (2006.01)
  *C10G 57/00* (2006.01)
  *C10G 57/02* (2006.01)
  *C10G 9/00* (2006.01)

(52) U.S. Cl.
  CPC .............. *C07C 2/84* (2013.01); *C10G 9/00* (2013.01); *C10G 50/00* (2013.01); *C10G 57/00* (2013.01); *C10G 57/02* (2013.01); *Y02P 20/52* (2015.11)

(56) References Cited

U.S. PATENT DOCUMENTS

| | | |
|---|---|---|
| 2,673,221 A | 3/1954 | Schrader et al. |
| 2,880,592 A | 4/1959 | Davison et al. |
| 2,926,751 A | 3/1960 | Kohl et al. |
| 2,943,125 A | 6/1960 | Ziegler et al. |
| 3,128,317 A | 4/1964 | Arkell et al. |
| 3,413,817 A | 12/1968 | Kniel |
| 3,459,678 A | 8/1969 | Hagemeyer et al. |
| 3,584,071 A | 6/1971 | Mcnulty et al. |
| 3,596,473 A | 8/1971 | Steich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,862,257 A | 1/1975 | Buben et al. |
| 3,900,526 A | 8/1975 | Johnson et al. |
| 3,931,349 A | 1/1976 | Kuo |
| 4,012,452 A | 3/1977 | Frampton |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,314,090 A | 2/1982 | Shewbart et al. |
| 4,329,530 A | 5/1982 | Irvine et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,433,185 A | 2/1984 | Tabak |
| 4,440,956 A | 4/1984 | Couvillion |
| 4,465,887 A | 8/1984 | Schammel |
| 4,481,305 A | 11/1984 | Jorn et al. |
| 4,489,215 A * | 12/1984 | Withers .............. B01J 23/08 585/415 |
| 4,554,395 A | 11/1985 | Jones et al. |
| 4,567,307 A | 1/1986 | Jones et al. |
| 4,629,718 A | 12/1986 | Jones et al. |
| 4,751,336 A | 6/1988 | Jezl et al. |
| 4,754,091 A | 6/1988 | Jezl et al. |
| 4,754,093 A | 6/1988 | Jezl et al. |
| 4,777,313 A | 10/1988 | Sofranko et al. |
| 4,814,539 A | 3/1989 | Jezl et al. |
| 4,822,944 A | 4/1989 | Brazdil et al. |
| 4,849,571 A | 7/1989 | Gaffney |
| 4,882,400 A | 11/1989 | Dumain et al. |
| 4,895,823 A | 1/1990 | Kolts et al. |
| 4,900,347 A | 2/1990 | McCue et al. |
| 4,939,311 A | 7/1990 | Washecheck et al. |
| 4,939,312 A | 7/1990 | Baerns et al. |
| 4,962,261 A | 10/1990 | Abrevaya et al. |
| 4,966,874 A | 10/1990 | Young et al. |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,041,405 A | 8/1991 | Lunsford et al. |
| 5,057,638 A | 10/1991 | Sweeney |
| 5,066,629 A | 11/1991 | Lukey et al. |
| 5,080,872 A | 1/1992 | Jezl et al. |
| 5,118,898 A | 6/1992 | Tyler et al. |
| 5,132,472 A | 7/1992 | Durante et al. |
| 5,137,862 A | 8/1992 | Mackrodt et al. |
| 5,179,056 A | 1/1993 | Bartley |
| 5,196,634 A | 3/1993 | Washecheck et al. |
| 5,198,596 A | 3/1993 | Kaminsky et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,371,306 A | 12/1994 | Woo et al. |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A * | 10/1995 | Wood .............. B01D 53/14 585/809 |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,712,217 A | 1/1998 | Choudhary et al. |
| 5,714,657 A | 2/1998 | deVries |
| 5,715,657 A | 2/1998 | Mondani et al. |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,866,737 A | 2/1999 | Hagemeyer et al. |
| 5,877,363 A | 3/1999 | Gildert et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Trubenbach et al. |
| 5,936,135 A | 8/1999 | Choudhary et al. |
| 5,959,170 A | 9/1999 | Withers |
| 6,020,533 A | 2/2000 | Lewis et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,146,549 A | 11/2000 | Mackay et al. |
| 6,153,149 A | 11/2000 | Rabitz et al. |
| 6,221,986 B1 | 4/2001 | Commereuc et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,447,745 B1 | 9/2002 | Feeley et al. |
| 6,509,292 B1 | 1/2003 | Blankenship et al. |
| 6,518,476 B1 | 2/2003 | Culp et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |

(56) References Cited

U.S. PATENT DOCUMENTS

| | | |
|---|---|---|
| 6,683,019 B2 | 1/2004 | Gartside et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,821,500 B2 | 11/2004 | Fincke et al. |
| 6,841,708 B1 | 1/2005 | Benje |
| 6,891,001 B2 | 5/2005 | Kuhlburger |
| 7,093,445 B2 | 8/2006 | Corr, II et al. |
| 7,157,612 B2 | 1/2007 | Ewert et al. |
| 7,176,342 B2 | 2/2007 | Bellussi et al. |
| 7,183,451 B2 | 2/2007 | Gattis et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,728,186 B2 | 6/2010 | Iaccino et al. |
| 7,781,636 B2 | 8/2010 | Iaccino et al. |
| 7,795,490 B2 | 9/2010 | Iaccino et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,071,836 B2 | 12/2011 | Butler |
| 8,080,215 B2 | 12/2011 | Taheri et al. |
| 8,129,305 B2 | 3/2012 | Bagherzadeh et al. |
| 8,153,851 B2 | 4/2012 | Gartside et al. |
| 8,163,070 B2 | 4/2012 | Hees et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,435,920 B2 | 5/2013 | White et al. |
| 8,450,546 B2 | 5/2013 | Chinta et al. |
| 8,552,236 B2 | 10/2013 | Iaccino et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,759,598 B2 | 6/2014 | Hayashi et al. |
| 8,796,497 B2 | 8/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 9,133,079 B2 | 9/2015 | Weinberger et al. |
| 9,321,702 B2 | 4/2016 | Nyce et al. |
| 9,334,204 B1 | 5/2016 | Radaelli et al. |
| 9,352,295 B2 | 5/2016 | Rafique et al. |
| 9,469,577 B2 | 10/2016 | Schammel et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 2002/0015670 A1 | 2/2002 | Shah et al. |
| 2003/0033932 A1 | 2/2003 | Sirkar et al. |
| 2003/0072700 A1 | 4/2003 | Goebel et al. |
| 2003/0189202 A1 | 10/2003 | Li et al. |
| 2003/0233019 A1 | 12/2003 | Sherwood |
| 2004/0220053 A1 | 11/2004 | Bagherzadeh et al. |
| 2005/0065391 A1 | 3/2005 | Gattis et al. |
| 2005/0065392 A1 | 3/2005 | Peterson et al. |
| 2006/0155157 A1 | 7/2006 | Zarrinpashne et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2008/0141713 A1 | 6/2008 | Verma |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian, Jr. et al. |
| 2009/0277837 A1 | 11/2009 | Liu et al. |
| 2010/0000153 A1 | 1/2010 | Kurkjian et al. |
| 2010/0003179 A1 | 1/2010 | Katusic et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0052466 A1 | 3/2011 | Liu |
| 2011/0124488 A1 | 5/2011 | Neltner et al. |
| 2011/0160508 A1 | 6/2011 | Ma et al. |
| 2011/0189559 A1 | 8/2011 | De Miranda et al. |
| 2011/0240926 A1 | 10/2011 | Schellen et al. |
| 2011/0257453 A1 | 10/2011 | Chinta et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2013/0023079 A1 | 1/2013 | Kang et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0178680 A1 | 7/2013 | Ha et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2014/0012053 A1 | 1/2014 | Iyer et al. |
| 2014/0018589 A1 | 1/2014 | Iyer et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0171707 A1 | 6/2014 | Nyce et al. |
| 2014/0181877 A1 | 6/2014 | Haykinson et al. |

(56) References Cited

U.S. PATENT DOCUMENTS

| | | |
|---|---|---|
| 2014/0194663 A1 | 7/2014 | Butler |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0378728 A1 | 12/2014 | Davis et al. |
| 2015/0010467 A1 | 1/2015 | Ito et al. |
| 2015/0152025 A1 | 6/2015 | Cizeron et al. |
| 2015/0210610 A1 | 7/2015 | Rafique et al. |
| 2015/0232395 A1 | 8/2015 | Nyce et al. |
| 2015/0307415 A1 | 10/2015 | Rafique et al. |
| 2015/0321974 A1 | 11/2015 | Schammel et al. |
| 2015/0368167 A1 | 12/2015 | Weinberger et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |

FOREIGN PATENT DOCUMENTS

| | | |
|---|---|---|
| CN | 101224432 A | 7/2008 |
| CN | 101387019 A | 3/2009 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| EP | 0253522 A2 | 1/1988 |
| EP | 303438 A2 | 2/1989 |
| EP | 0608447 A1 | 8/1994 |
| EP | 0634211 A1 | 1/1995 |
| EP | 0722822 A1 | 7/1996 |
| EP | 0716064 B1 | 7/1998 |
| EP | 1110930 A1 | 6/2001 |
| EP | 0761307 B1 | 2/2003 |
| EP | 0764467 B1 | 2/2003 |
| EP | 1632467 A1 | 3/2006 |
| EP | 1749807 A1 | 2/2007 |
| EP | 1749806 B1 | 10/2008 |
| FR | 649429 A | 12/1928 |
| GB | 733336 A | 7/1955 |
| JP | 2005/161225 A | 6/2005 |
| WO | 8607351 A1 | 12/1986 |
| WO | WO 02/04119 A1 | 1/2002 |
| WO | WO 2004/033488 A2 | 4/2004 |
| WO | WO 2004/056479 A1 | 7/2004 |
| WO | WO 2004/103936 A1 | 12/2004 |
| WO | WO 2005/067683 A2 | 7/2005 |
| WO | WO 2007/030515 A2 | 11/2007 |
| WO | WO 2007/130515 A2 | 11/2007 |
| WO | WO 2008/005055 A2 | 1/2008 |
| WO | WO 2008/014841 A1 | 2/2008 |
| WO | WO 2008/022147 A1 | 2/2008 |
| WO | WO 2008/073143 A2 | 6/2008 |
| WO | WO 2009/071463 A2 | 6/2009 |
| WO | WO 2009/074203 A1 | 6/2009 |
| WO | WO 2009/115805 A1 | 9/2009 |
| WO | 2010005453 A2 | 1/2010 |
| WO | WO 2011/008464 A1 | 1/2011 |
| WO | WO 2011/041184 A2 | 4/2011 |
| WO | WO 2011/050359 A1 | 4/2011 |
| WO | WO 2010/069488 A8 | 5/2011 |
| WO | WO 2011/149996 A2 | 12/2011 |
| WO | WO 2012/162526 A2 | 11/2012 |
| WO | 2013177433 A2 | 11/2013 |
| WO | WO 2013/177461 A2 | 11/2013 |
| WO | 2014049445 A2 | 4/2014 |
| WO | 2014143880 A1 | 9/2014 |
| WO | 2015105911 A1 | 7/2015 |
| WO | 2015106023 A1 | 7/2015 |

OTHER PUBLICATIONS

Wang et al. Critical Influence of BaCO3 on Low Temperature Catalytic Activity of BaCO3/ZrO2 Catalysts for Oxidative Coupling of Methane. Catalysis Letters (2009) 129: 156-162.*

U.S. Appl. No. 14/591,850, filed Jan. 7, 2015, Nyce et al.

U.S. Appl. No. 14/592,668, filed Jan. 8, 2015, Rafique et al.

Barrett, et al. The determination of pore volume and area distributions in porous substances—Compuatations from nitrogen isotherms. J. Am. Chem. Soc., 1951, vol. 73, pp. 373-380.

Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.

Chen, et al. M2 Forming—A Process for Aromatization of Light Hydrocarbons. Ind. Eng. Chem. Process. Des. Dev. 1986, 25, 151-155.

Li, et al. Combined Single-Pass Conversion of Methane Via Oxidative Coupling and Dehydroaromatization. Catalysis Letters, Sep. 2003, vol. 89, Issue 3-4, pp. 275-279.

Nielsen, et al. Treat LPGs with amines. Hydrocarbon Process 79 (1997): 49-59.

Saito, et al. Dehydrogenation of Propane Over a Silica-Supported Gallium Oxide Catalyst. Catalysis Letters, Sep. 2003, vol. 89, Issue 3-4, pp. 213-217.

Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.

Xu, et al. Maximise ethylene gain and acetylene selective hydrogenation efficiency. Petroleum technology quarterly 18.3 (2013): 39-42.

Zhou. BP-UOP Cyclar Process. Handbook of Petroleum Refining Processes, The McGraw-Hill Companies (2004), pp. 2.29-2.38.

International Search Report and Written Opinion dated Mar. 17, 2014 for PCT/US2013/021312.

Nghiem, XS "Ethylene Production by Oxidative Coupling of Methane: New Process Flow Diagram based on Adsorptive Separation" Berlin, Mar. 14, 2014.

Nyce, G. et al. PCT/US2015/010525 filed Jan. 7, 2015 for "Ethylene-to-Liquids Systems and Methods".

Rafique, H. et al. PCT/US2015/010688 filed Jan. 8, 2015 for "Oxidative Coupling of Methane Implementations for Olefin Production".

Sheridan, D. et al. PCT/US2014/067465 filed Nov. 25, 2014 for "Integrated Mixers and Heat Exchangers for Oxidative Coupling Methane Systems".

Guo, X. et al. "Direct, Nonoxidative Conversion of Methane to Ethylene, Aromatics, and Hydrogen" Science (2014) 344:616-619.

International search report and written opinion dated Jun. 12, 2015 for PCT Application No. US2015/010688.

Kaminsky, M.P. et al. "Deactivation of Li-Based Catalysts for Methane Oxidative Coupling" Poster ACS Symposium on Natural Gas Upgrading II (Apr. 5-10, 1992).

Kaminsky, M.P. et al. "Oxygen X-Ray Absorption Near-Edge Structure Characterization of the Ba-Doped Yttria Oxidative Coupling Catalyst" J Catalysis (1992) 136:16-23.

Lunsford, J.H. "Catalytic conversion of methane to more useful chemicals and fuels: a challenge for the 21st century" Catalysis Today (2000) 63:165-174.

Mimoun, H. et al. "Oxypyrolysis of Natural Gas" Appl Catalysis (1990) 58:269-280.

Notice of Allowance dated Jun. 8, 2015 for U.S. Appl. No. 13/739,954.

Radaelli, G. et al. "Efficient Oxidative Coupling of Methane Processes and Systems" U.S. Appl. No. 14/789,953, filed Jul. 1, 2015.

Rafique, H. et al. "Oxidative Coupling of Methane Implementations for Olefin Production" U.S. Appl. No. 14/789,946, filed Jul. 1, 2015.

Schammel, W.P. et al. "Oxidative Coupling of Methane Systems and Methods" U.S. Appl. No. 14/789,901, filed Jul. 1, 2015.

(56) References Cited

OTHER PUBLICATIONS

"Water Electrolysis & Renewable Energy Systems" FuelCellToday (May 2013).
Berstad, D. et al., "Low-temperature CO2 removal from natural gas" Energy Procedia (2012) 26:41-48.
Graves, C.R. "Recycling CO2 into Sustainable Hydrocarbon Fuels: Electrolysis of CO2 and H2O" Dissertation, Columbia University (2010).
Gupta, M. "Review on Heat Recovery Unit with Thermoelectric Generators" Intl J Eng and Innov Tech (IJEIT) (2014) 4(4):128-131.
Kaibe, H. et al. "Recovery of Plant Waste Heat by a Thermoelectric Generating System" Komatsu Tech Report (2011) 57(164):26-30.
Li, B. et al. "Advances in CO2 capture technology: A patent review" Applied Energy (2013) 102:1439-1447.
Office action dated Sep. 11, 2015 for U.S. Appl. No. 14/789,946.
Office action dated Sep. 11, 2015 for U.S. Appl. No. 14/789,953.
Ohashi, Y. et al. "Development of Carbon Dioxide Removal System from the Flue Gas of Coal Fired Power Plant" Energy Procedia (2011) 4:29-34.
Seeberger, A. et al. "Gas Separation by Supported Ionic Liquid Membranes" DGMK-Conference, Hamburg, Germany (2007).
Simons, K. "Membrane Technologies for CO2 Capture" Dissertation, U. of Twente (2010).
Suzuki, K. "Toshiba's Activity in Clean Coal and Carbon Capture Technology for Thermal Power Plants" APEC Clean Fossil Energy Technical and Policy Seminar (Feb. 22, 2012).
Weinberger, S. et al. "Process for Separating Hydrocarbon Compounds" U.S. Appl. No. 14/820,460, filed Aug. 6, 2015.
Witek-Krowiak, A. et al. "Carbon Dioxide Removal in a Membrane Contactor-Selection of Absorptive Liquid/Membrane System" Intl J Chem Eng and Appl. (2012) 3(6):391-395.
Xu, G. et al. "An Improved CO2 Separation and Purification System Based on Cryogenic Separation and Distillation Theory" Energies (2014) 7:3484-3502.
Yan, D. "Modeling and Application of a Thermoelectric Generator" Thesis, Univ. Toronto (2011).
Duggal, S. et al. "Advanced Oxidative Coupling of Methane" U.S. Appl. No. 14/868,911, filed Sep. 29, 2015.
International search report and written opinion dated Nov. 11, 2015 for PCT Application No. US2014/067465.
Office action dated Nov. 2, 2015 for U.S. Appl. No. 14/789,901.
Office action dated Nov. 13, 2015 for U.S. Appl. No. 13/900,898.
Smith, et al. Recent developments in solvent absorption technologies at the CO2CRC in Australia. Energy Procedia 1 (2009): 1549-1555.
U.S. Appl. No. 13/115,082, filed May 24, 2011, Scher et al.
U.S. Appl. No. 13/479,767, filed May 24, 2012, Cizeron et al.
U.S. Appl. No. 13/689,611, filed Nov. 29, 2012, Zurcher et al.
U.S. Appl. No. 13/901,319, filed May 23, 2013, Cizeron et al.
U.S. Appl. No. 14/099,614, filed Dec. 6, 2013, Nyce et al.
U.S. Appl. No. 14/212,435, filed Mar. 14, 2014, Schammel et al.
U.S. Appl. No. 14/553,795, filed Nov. 25, 2014, Cizeron et al.
U.S. Appl. No. 61/669,523, filed Jul. 9, 2012, Iyer et al.
U.S. Appl. No. 61/773,669, filed Mar. 6, 2013, Iyer et al.
U.S. Appl. No. 61/794,486, filed Mar. 15, 2013, Schammel et al.
U.S. Appl. No. 62/050,729, filed Sep. 15, 2014, Rafique et al.
U.S. Appl. No. 62/073,478, filed Oct. 31, 2014, Rafique et al.
Bollmann, et al. Ethylene tetramerization: a new route to produce 1-octene in exceptionally high selectivities. J Am Chem Soc. Nov. 17, 2004;126(45):14712-3.
Carter, et al. High activity ethylene trimerisation catalysts based on diphosphine ligands. Chem Commun (Camb). Apr. 21, 2002;(8):858-9.
Chemsystems PERP Report Ethylene Oxide/Ethylene Glycol 2005.
Choudhary, et al. Microporous and Mesoporous Materials. 2001. 253-267.
International search report dated Mar. 19, 2014 for PCT Application No. US2013/073657.
Knuuttila, et al. Advanced Polyethylene Technologies—Controlled Material Properties. Long Term Properties of Polyolefins Advances in Polymer Science vol. 169, 2004, pp. 13-28.
Li, et al. Energy and Fuels. 2008, 22: 1897-1901.
Natural Gas Spec Sheet, 2003, prepared by Florida Power and Light Company.
Nexant/Chemsystems HDPE Report, PERP 09/10-3, Jan. 2011.
Olah, G. Hydrocarbon Chemistry. 2nd Edition, John Wiley & Sons, 2003.
Zhang, Q. Journal of Natural Gas Chem., 12:81, 2003.
U.S. Appl. No. 61/489,651, filed May 24, 2011, Cizeron et al.
U.S. Appl. No. 61/564,832, filed Nov. 29, 2011, Cizeron et al.
U.S. Appl. No. 61/564,834, filed Nov. 29, 2011, Zurcher et al.
U.S. Appl. No. 61/564,836, filed Nov. 29, 2011, Nyce et al.
U.S. Appl. No. 61/651,399, filed May 24, 2012, Zurcher et al.
U.S. Appl. No. 61/651,485, filed May 24, 2012, Schammel et al.
U.S. Appl. No. 61/791,312, filed May 15, 2013, Schammel et al.
Autothermal Partial Oxidative Coupling of Methane. IP.com, Prior Art Database Technical Disclosure, Jul. 29, 2008, 5 pages.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted $La_2O_3$ Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Cizeron, et al. Catalytic forms and formulations. U.S. Appl. No. 13/901,319, filed May 23, 2013, 132 pages.
Debart, et al. $\alpha$-$MNO_2$ Nanowires: A catalyst for the $O_2$ Electrode in Rechargeabl Lithium Batteries. Angewandte Chemie International Edition 47: 4521-4524, 2008.
Enger, et al. A review of catalytic partial oxidation of methane to synthesis gas with emphasis on reaction mechanisms over transition metal catalysts. Applied Catalysis A: General 346 (1-2): 1-27, Aug. 2008.
Gao, et al. A study on methanol steam reforming to $CO_2$ and $H_2$ over the $La_2CO_4$ nanofiber catalyst. Journal of Solid State Chemistry 181: 7-13, 2008.
Gao, et al. The direct decomposition of NO over the $La_2CuO_4$ nanofiber catalyst. Journal of Solid State Chemistry 181: 2804-2807, 2008.
Guo, et al. Current Status and Some Perspectives of Rare Earth Catalytic Materials. Journal of The Chinese Rare Earth Society 25(1): 1-15, Feb. 2007.
Huang, et al. Exploiting shape effects of La2O3 nanocrystals for oxidative coupling of methane reaction. Nanoscale—Electronic Supplementary Material, 2013, 7 pages.
Huang, et al. Exploiting shape effects of $La_2O_3$ nanocrystals for oxidative coupling of methane reaction. Nanoscale 5(22): 10844-10848, 2013.
International search report and written opinion dated Mar. 6, 2014 for PCT/US2013/042480.
Keller, et al. Synthesis of Ethylene via Oxidative Coupling of Methane. Journal of Catalysis 73: 9-19, 1982.
Kuang, et al. Grafting of PEG onto lanthanum hydroxide nanowires. Materials Letters 62:4078-4080, 2008.
Ling, et al. Preparation of Ag core—A Ushell Nanowires and Their Surface Enhanced Raman Spectroscopic Studies. Acta Chimica Sinica. 65 (9): 779-784, 2007.
Liu, et al. A novel $Na_2WO_4$—Mn.SiC monolithic foam catalyst with improved thermal properties for the oxidative coupling of methane. Catalysis Communications 9: 1302-1306, 2008.
Mleczko, et al. Catalytic oxidative coupling of methane—reaction engineering aspects and process schemes. Fuel Processing Technology 42:217-248, 1995.

(56) References Cited

OTHER PUBLICATIONS

Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Niu, et al. Preparation and characterization of $La_2O_3CO_3$ nanowires with high surface areas. Jounral of the Chinese Rare Earth Society 23 (Spec. Issue): 33-36, Dec. 2005.
Nyce, et al. Integrated processes and systems for conversion of methane to multiple high hydrocarbon products. U.S. Appl. No. 14/099,614, filed Dec. 6, 2013, 67 pages.
Nyce, et al. Polymer template nanowire catalysts. U.S. Appl. No. 61/564,836, filed Nov. 29, 2011, 317 pages.
Office action dated Oct. 23, 2014 for U.S. Appl. No. 13/739,954.
Pak, et al. Elementary Reactions in the Oxidative Coupling of Methane over $Mn/NA_2 WO4/SiO_2$ and $MN/NA_2 WO4/MgO$ Catalysts. Journal of Catalysis 179:222-230, 1998.
Qiu, et al. Steady-state conversion of methane to aromatics in high yields using an integrated recycle reaction system. Catalysis Letters 48: 11-15, 1997.
Schammel, et al. Catalysts for petrochemical catalysis. U.S. Appl. No. 61/794,486, filed Mar. 15, 2013, 217 pages.
Schweer, et al. OCM in a fixed bed reactor: limits and perspectives. Catalysis Today, vol. 21, No. 2-3, Dec. 1, 1994, pp. 357-369.
Somorjai, et al. High technology catalysts towards 100% selectivity Fabrication, characterization and reaction studies. Catalysis today 100:201-215, 2005.
Takanabe, et al. Mechanistic Aspects and Reaction Pathways for Oxidative Coupling of Methane on $Mn/NA_2 WO4/SiO_2$ Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by $Mn/NA_2 WO4/SiO_2$. Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Wang, et al. Autothermal oxidative coupling of methane on the $SrCO_3/Sm_2O_3$ catalysts. Catalysis communications 10: 807-810, 2009.
Wang, et al. Comparative study on oxidation of methane to ethane and ethylene over $NA_2 WO4$—$Mn/SiO_2$ catalysts prepared by different methods. Journal of Molecular Catalysis A: Chemical 245:272-277, 2006.
Wang, et al. Low temperature selective oxidation of methane to ethane and ethylene over $BaCO_3/La_2O_3$ catalysts prepared by urea combustion method. Catalysis communications 7: 5963, 2006.
Wong, et al. Oxidative coupling of methane over alkali metal oxide promoted $La_2O_3/BaCO_3$ cataylsts. J. Chem. Tech. Biotechnol. 65:351-354, 1996.
Yang, et al. Anistropic synthesis of boat shaped core shell Au—Ag nanocrystals and nanowires. Nanotechnology 17: 2304-2310, 2006.
Yu, et al. Oxidative coupling of methane over acceptor-doped SrTi $O_3$: Correlation between p-type conductivity and $C_2$ selectivity and $C_2$ yield. Journal of Catalysis. 13 (5): 338-344, 1992.
Zhao, et al. Technologies and catalysts for catalytic preparation of ethene. Industrial catalysis 12 (Supplement): 285-289, 2004.
Zhou, et al. Functionalization of lanthanum hydroxide nanowires by atom transfer radical polymerization. Nanotechnology 18, 2007, 7 pages.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
International search report and written opinion dated Nov. 1, 2013 for PCT/US2013/049742.
U.S. Appl. No. 13/936,870, filed Jul. 8, 2013, Iyer et al.
Cavani, et al. Oxidative dehydrogenation of ethane and propane: How far from commercial implementation? Catalysis Today. 2007; 127(1-4):113-131.
Labinger. Oxidative coupling of methane: an inherent limit to selectivity? Catal. Lett. 1988; 1:371-376.
Lunsford. The Catalytic Oxidative Coupling of Methane. Angew. Chem Int. Ed. Engl. 1995; 34:970-980.
International preliminary report on patentability dated Jul. 21, 2016 for PCT Application No. US2015/010688.
International search report and written opinion dated Aug. 11, 2016 for PCT/US2016/024195.
International search report and written opinion dated Aug. 18, 2016 for PCT/US2016/022891.
Notice of allowance dated Aug. 9, 2016 for U.S. Appl. No. 15/076,480.
Notice of allowance dated Aug. 11, 2016 for U.S. Appl. No. 13/900,898.
Notice of allowance dated Aug. 22, 2016 for U.S. Appl. No. 14/820,460.
Office action dated Jul. 29, 2016 for U.S. Appl. No. 14/789,901.
European search report and search opinion dated Jan. 20, 2016 for EP Application No. 13817389.3.
Notice of allowance dated Jan. 4, 2016 for U.S. Appl. No. 14/789,953.
Notice of allowance dated Jan. 13, 2016 for U.S. Appl. No. 14/789,946.
Office action dated Jan. 14, 2016 for U.S. Appl. No. 13/936,870.
Oil Refinery—Wikipedia, The Free Encyclopedia Website. Jan. 2009.
American Petroleum Institute Publication 534 "Heat Recovery Steam Generators" Jan. 1995 (51 pages).
Co-pending U.S. Appl. No. 15/076,402, filed Mar. 21, 2016.
Co-pending U.S. Appl. No. 15/076,480, filed Mar. 21, 2016.
Notice of allowance dated Apr. 27, 2016 for U.S. Appl. No. 13/900,898.
Office action dated Apr. 22, 2016 for U.S. Appl. No. 15/076,402.
Office action dated Apr. 22, 2016 for U.S. Appl. No. 15/076.480.
Office action dated May 20, 2016 for U.S. Appl. No. 14/820,460.
Notice of allowance dated Sep. 22, 2016 for U.S. Appl. No. 13/936,870.
Notice of allowance dated Oct. 24, 2016 for U.S. Appl. No. 14/789,901.
Office action dated Mar. 16, 2016 for U.S. Appl. No. 14/789,901.
Fallah, et al., A New Nano-(2Li2O/MgO) Catalyst/Porous Alpha-Alumina Composite for the Oxidative Coupling of Methane Reaction, AlChE Journal, Mar. 2010, 56(3):717-28.
International search report and written opinion dated Feb. 2, 2017 for PCT Application No. US-2016052959.
Office action dated Jan. 26, 2017 for U.S. Appl. No. 15/341,551.
Co-pending U.S. Appl. No. 15/341,551, filed Nov. 2, 2016.
Co-pending U.S. Appl. No. 15/354,886, filed Nov. 17, 2016.
Co-pending U.S. Appl. No. 15/356,202, filed Nov. 18, 2016.
Co-pending U.S. Appl. No. 15/359,399, filed Nov. 22, 2016.
Office action dated Dec. 23, 2016 for U.S. Appl. No. 14/592,668.
Office action dated Mar. 6, 2017 for U.S. Appl. No. 13/936,870.

* cited by examiner

NATURAL GAS PROCESSING AND SYSTEMS

CROSS-REFERENCE

This application claims the benefit of U.S. Provisional Patent Application No. 61/773,669, filed Mar. 6, 2013 and U.S. Provisional Patent Application No. 61/669,523, filed Jul. 9, 2012, each of which is incorporated herein by reference in its entirety.

BACKGROUND

Technical Field

The present invention is directed to methods and processes for the conversion of natural gas to higher hydrocarbons. In particular, the present invention includes systems and facilities for natural gas processing.

Description of the Related Art

There exists a substantial infrastructure for petrochemical processing throughout the world. This infrastructure is deployed on virtually every habitable continent, addresses wide ranging industries, and employs a wide variety of different implementations of similar or widely differing technologies.

As a major constituent to this infrastructure, the gas industry itself involves multiple components from exploration, recovery, processing and conversion technologies in transforming natural gas into useful end products. The gas industry involves hundreds to thousands of processing and fractionation facilities in the United States alone. These facilities generally include all the requisite process equipment for processing and separating incoming natural gas into its constituent and valued components, the requisite gas delivery infrastructure, and storage and distribution infrastructure for a wide range of different products including liquid products.

Further processing, conversion and/or commercialization of these products involves still additional infrastructure. For example, conversion of ethane from gas to higher value chemicals, e.g., olefins, involves substantial infrastructure in the form of steam crackers, and their associated infrastructure. Similarly, in other geographies, olefin production relies upon the conversion of petroleum refining by products, or naphtha, through alternative cracking operations to produce ethylene and other olefins.

As will be appreciated, the capital costs associated with each of the facility types described above can run from tens of millions to hundreds of millions of dollars each. Additionally, there are inputs and outputs, of these facilities, in terms of both energy and materials, which have additional costs associated with them, both financial and otherwise, that could be further optimized in terms of cost and efficiency. Finally, because different facilities tend to be optimized for the particularities of the market in which they exist, they tend to be rather rigidly run, without the flexibility or optionality to optimize for the temporal realities of their given market, e.g., a particular oil or gas environment.

It would therefore be advantageous to be able to leverage existing processing infrastructure for new processing methods and systems without expending significant capital resources in retrofitting that infrastructure, optionally taking advantage of the different inputs and outputs of these facilities to create much greater value from the same or similar infrastructure, raw materials, and/or process flows. The present invention meets these and a variety of other needs.

SUMMARY

The invention relates to integrated processing facilities for producing higher hydrocarbons from natural gas and other hydrocarbon feedstocks. Provided are processing facilities or systems that include an integrated oxidative coupling of methane ("OCM") reactor system that provide various components of its OCM product, or other outputs, as an input to various systems in the processing facility, including, for example, extraction systems, fractionation systems and the like. Alternatively or additionally, integrated OCM reactor systems are provided that take up various product streams or outputs of different units or systems in these processing facilities.

In certain aspects, the invention provides natural gas processing systems that comprise an OCM reactor system comprising at least a first reactor vessel having at least a first OCM catalyst disposed therein. The systems also comprise one or more of an extraction system for separating at least one hydrocarbon compound from at least one non-hydrocarbon compound, and a fractionation system for separating at least two different hydrocarbon compounds. The systems further comprise an interconnected pipeline, the interconnected pipeline fluidly connecting one or more of an inlet or an outlet of the OCM reactor system to one or more of an inlet or an outlet of the one or more of the extraction system and the fractionation system.

In another related aspect, provided are natural gas processing systems and methods, comprising an OCM reactor system comprising at least a first reactor vessel having at least a first OCM catalyst disposed therein. The system also comprises an extraction system for separating at least one non-hydrocarbon compound from at least one hydrocarbon compound, and a fractionation system for separating at least two different hydrocarbon compounds. Also included is an interconnected pipeline, the interconnected pipeline fluidly connecting one or more of an inlet or an outlet of the OCM reactor system to one or more of an inlet or an outlet of one or more of the fractionation system and the extraction system.

Also provided are methods and systems for producing hydrocarbon compounds. The methods comprise contacting methane and air/oxygen with an OCM catalyst under OCM reaction conditions in a first reactor system to produce an OCM product, the OCM product comprising two or more different hydrocarbon compounds. The OCM product produced in the contacting step is then transferred to a fractionation system fluidly coupled to the first reactor system. At least one hydrocarbon compound in the OCM product is then separated from at least one other hydrocarbon compound in the OCM product in the fractionation system.

In a similar aspect, the invention provides methods and systems for producing hydrocarbon compounds, comprising contacting methane and air/oxygen with an OCM catalyst under OCM reaction conditions in a first reactor system to produce an OCM product, the OCM product comprising one or more hydrocarbon compounds and at least one non-hydrocarbon compound. The OCM product produced in the contacting step is transferred to an extraction system fluidly coupled to the first reactor system. At least one hydrocarbon compound in the OCM product is separated from at least one other hydrocarbon or non-hydrocarbon compound in the OCM product.

Also provided are integrated hydrocarbon processing systems that include both a steam cracker configured to convert one or more saturated hydrocarbons into one or more unsaturated hydrocarbons, and an OCM reactor system configured to convert methane to ethylene. These two systems are both fluidly connected at their outlets to the inlet of an integrated hydrocarbon fractionation system such that $C_2+$ containing streams from each of the steam cracker and OCM reactor system are passed into the fractionation system.

In a similar aspect, provided are methods for producing one or more desired hydrocarbon compounds, comprising directing a first hydrocarbon feedstock comprising saturated hydrocarbons to a steam cracker to produce an unsaturated hydrocarbon containing stream. These methods also include directing a second hydrocarbon feedstock comprising methane to an OCM reactor system to produce an ethylene containing stream. The resulting streams, e.g., the unsaturated hydrocarbon containing stream and the ethylene containing stream, are then both directed to an integrated fractionation system, e.g., a common integrated fractionation system, to produce one or more desired hydrocarbon product streams.

Relatedly, also provided are methods and systems for producing hydrocarbon compounds, comprising contacting methane and air/oxygen with an OCM catalyst under OCM reaction conditions in a first reactor system to produce an OCM product, the OCM product comprising one or more different hydrocarbon compounds. The OCM product produced in the contacting step is transferred to an integrated oligomerization system to produce one or more higher hydrocarbon compounds from the one or more hydrocarbon compounds in the OCM product. The one or more higher hydrocarbons produced in the oligomerization system are then transferred to a fractionation system fluidly coupled to the oligomerization system for separating at least one hydrocarbon compound in the OCM product from at least one higher hydrocarbon.

In another aspect, provided are natural gas processing systems and methods, comprising an OCM reactor system for processing natural gas to produce an OCM product, the OCM reactor system comprising a thermal energy extraction system thermally coupled to the OCM reactor system for removing thermal energy from the OCM reactor system. The system also includes a natural gas fractionation unit for separating one or more hydrocarbon components in one or more of natural gas or the OCM product from at least one other hydrocarbon product in the natural gas or OCM product. Also included are one or more heat exchangers thermally coupled to each of the thermal energy extraction system and the fractionation unit, to convey thermal energy from the thermal energy extraction system to the fractionation unit to heat the natural gas or OCM product in the fractionation unit to separate the one or more hydrocarbon components in the natural gas or OCM product from at least one other hydrocarbon product in the natural gas or OCM product.

In still another aspect, provided are natural gas processing systems and methods, comprising an extraction system for separating methane from NGLs in natural gas, the extraction system having a methane rich effluent outlet, and further comprising an OCM reactor system comprising an inlet fluidly coupled to the methane rich effluent outlet of the extraction system. The system also comprises a thermal energy removal system for removing thermal energy from the OCM reactor system, and a heat exchanger thermally coupled to each of the thermal energy removal system and a fluid connection between the methane rich effluent outlet and the OCM reactor inlet, for heating a methane rich effluent from the extraction system to greater than 400° C.

In alternative or additional aspects, provided are natural gas processing systems and methods, comprising an OCM reactor system, a steam generator thermally coupled to the OCM reactor, to generate steam from thermal energy produced by the OCM reactor, and an electrical generator coupled to the steam generator for generating electricity from steam produced by the steam generator.

In further alternative or additional aspects, provided are methods and systems for collecting $CO_2$, comprising, in an OCM reactor system, contacting methane and air/oxygen with an OCM catalyst under OCM reaction conditions to produce a product stream comprising one or more hydrocarbon compounds and $CO_2$, separating $CO_2$ from the one or more hydrocarbon compounds in the product stream in an extraction system integrated with the OCM reactor system, and collecting the $CO_2$ separated from the product stream.

DETAILED DESCRIPTION

Figure 1:
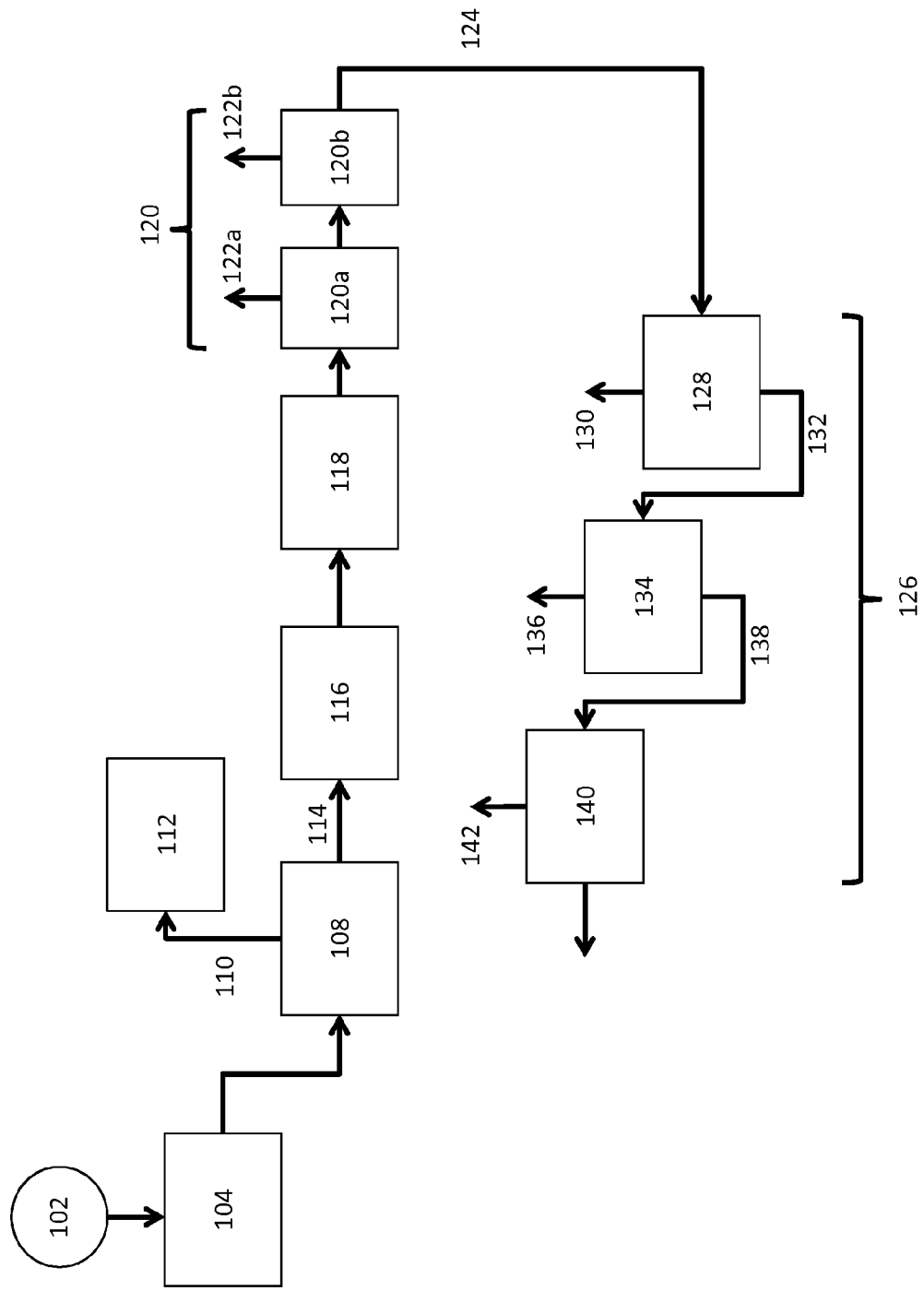
FIG. 1 schematically illustrates an exemplary natural gas processing facility.

I. Integration of OCM in Gas and Petrochemical Processing

Embodiments of the present invention provide for the integration of oxidative coupling of methane ("OCM") and optionally, oxidative dehydrogenation of ethane to ethylene or propane to propylene ("ODH") processes and systems into existing natural gas and other petrochemical processes and facilities in order to gain advantages of feedstock flexibility, energy efficiency, and flexibility to better define the resulting product slates from those processes. In particular, by providing an integrated OCM process with other processes, one can take advantage of the complementarity of the OCM processes with these other gas or petrochemical processes to improve one or all of feedstock flexibility, product slate flexibility, energy efficiency, and other process parameters. While this integration provides benefits to a number of different processes and systems, for ease of illustration, it is described in greater detail with respect to integration into existing natural gas NGL processes, as well as olefin production processes from ethane, ethane/propane, and/or naphtha.

II. Natural Gas Processing

As compared to crude oil, natural gas is in relatively abundant supply, particularly in accessible and available locations, such as in North America. When viewed at a national level, the gas reserves within the United States are among the largest in the world, providing not only a highly valued natural resource, but also providing the potential for greater energy independence for the country. Exploitation of those reserves, however, poses challenges distinct from those faced and managed by the oil industry. In particular, large-scale transport of natural gas is typically accomplished by pipeline, which creates expensive infrastructure requirements. Long-distance gas pipelines require consistent and predictable qualities of gas in order to function economically and safely. For example the energy density and vapor pressure of the gas to be moved long distance must fall within a predetermined specification. As a result, the gas industry has resorted to building processing facilities close to gas fields at which raw incoming natural gas containing impurities such as $CO_2$, $N_2$, water, regulated compounds such as heavy metals, and valuable components including $C_1$, $C_2$, $C_3$, $C_4$, and $C_5+$ is separated into more manageable gases and liquids that can, for example, be transported by less costly and more appropriate means, e.g., common-carrier pipeline, rail, truck, etc.

These facilities typically take in natural gas, which is, depending upon the source of the gas, typically comprised of a mixture of varying amounts of methane, higher hydrocarbons, water vapor, hydrogen sulfide ($H_2S$), carbon dioxide, helium, nitrogen, and other compounds.

Natural gas processing typically involves separating all of the various impurities, higher hydrocarbons and fluids from the gas, to produce what is known as 'pipeline quality' dry natural gas. Major transportation pipelines usually impose restrictions on the make-up of the natural gas that is allowed into the pipeline. That means that before the natural gas can be transported it must be appropriately treated to meet the requirements of the pipeline. The ethane, propane, butane, pentanes and other higher hydrocarbons that are removed from this natural gas, known as 'natural gas liquids' (NGLs) are very valuable by-products of natural gas processing, and are therefore also recovered in these facilities. NGLs include ethane, propane, butane, iso-butane, and natural gasoline. These NGLs are sold separately from the pipeline ready gas, and have a variety of different uses; including providing raw materials for oil refineries or petrochemical plants, and as sources of energy, while other separated components are used in other applications, e.g., for enhancing oil recovery.

While some of the needed processing can be accomplished at or near the gas wellhead (field processing), as noted above, the complete processing of natural gas typically takes place at one or more processing plants that are usually located within the natural gas producing region. The extracted natural gas is transported to these processing plants through a network of gathering pipelines, which are small-diameter, low-pressure pipes. A complex gathering system can include thousands of miles of pipes, interconnecting the processing plant to upwards of 100 wells in the area.

In addition to processing done at the wellhead and at centralized processing plants, some additional processing is also sometimes accomplished at 'straddle extraction plants'. These plants are typically located on major pipeline systems. Although the natural gas that arrives at these straddle extraction plants is already of pipeline quality, in certain instances there may still exist small quantities of NGLs or other impurities, which are extracted at the straddle plants.

The actual practice of processing natural gas to pipeline dry gas quality levels can be quite complex, but usually involves four main processes to remove the various impurities: oil and condensate removal, water removal, glycol dehydration and solid desiccant dehydration. In addition to these four processes, heaters and scrubbers are often installed, usually at or near the wellhead. The scrubbers serve primarily to remove sand and other large-particle impurities. The heaters ensure that the temperature of the gas does not drop too low. With natural gas that contains even low quantities of water, natural gas hydrates have a tendency to form when temperatures drop. These hydrates are solid or semi-solid compounds, resembling ice like crystals, and their accumulation can impede the passage of natural gas through valves and gathering systems. To reduce the occurrence of hydrates, small natural gas-fired heating units are typically installed along the gathering pipe wherever it is likely that hydrates may form.

As noted, natural gas coming directly from a well contains many natural gas liquids that are commonly removed. Most NGLs must be removed to meet common carried pipeline specifications, often referred to as required extraction. When Natural gas liquids (NGLs) have sufficiently high values as separate products, it becomes economical to remove more than the minimum amount of NGLs contained in the gas stream, a scenario often referred to as discretionary extraction. The removal of natural gas liquids usually takes place in a relatively centralized processing plant, and uses techniques similar to those used to dehydrate natural gas. There are two basic steps to the treatment of natural gas liquids in the natural gas stream. First, the liquids must be extracted from the natural gas. Second, these natural gas liquids must be separated themselves, down to their base or more pure components.

A. NGL Extraction

As an initial matter, the NGLs must be extracted from the natural gas stream. In typical gas processing, there are two principle techniques for removing NGLs from the natural gas stream: the absorption method and the cryogenic expander process, also referred to as a cryogenic extraction or separation process. According to the Gas Processors Association, these two processes account for around 90 percent of total natural gas liquids production.

In NGL absorption, an absorbing oil that has an 'affinity' for NGLs is used in much the same manner as glycol, which has an affinity for water, when used in the dehydration process. Before the absorbing oil has picked up any NGLs, it is termed 'lean' absorption oil. As the natural gas is passed through an absorption tower, it is brought into contact with the absorption oil, which soaks up, or absorbs, a high proportion of the NGLs. The 'rich' absorption oil, now containing NGLs, exits the absorption tower through the bottom. It is now a mixture of absorption oil, propane, butanes, pentanes, and other heavier hydrocarbons. The rich oil is fed into lean oil stills, where the mixture is heated to a temperature above the boiling point of the NGLs, but below that of the oil. This process allows for the recovery of around 75 percent of butanes, and 85-90 percent of pentanes and heavier hydrocarbons from the natural gas stream.

The basic absorption process above can be modified to improve its effectiveness, or to target the extraction of specific NGLs. In the refrigerated oil absorption method, where the lean oil is cooled through refrigeration, propane recovery can be upwards of 90 percent, and around 40 percent of ethane can be extracted from the natural gas stream. Extraction of the other, heavier NGLs can be close to 100 percent using this process.

Cryogenic extraction processes are also used to extract NGLs from natural gas, and are in fact more commonly used today. While absorption methods can extract almost all of the heavier NGLs, the lighter hydrocarbons, such as ethane, are often more difficult to recover from the natural gas stream. In certain instances, it is economic to simply leave the lighter NGLs in the natural gas stream. However, if it is economic to extract ethane and other lighter hydrocarbons, cryogenic processes are required for high recovery rates. Essentially, cryogenic processes consist of dropping the temperature of the gas stream to around −120 degrees Fahrenheit. The condensed NGLs are then transported to subsequent processes while the gas components, e.g., methane and nitrogen and other gases, are taken off in gas form.

Thus, the extraction systems used in the invention typically operate both to separate non-hydrocarbon compounds, such as $CO_2$, $N_2$, and water from the hydrocarbon compounds, e.g., NGLs, but also function to de-methanize the gas stream, e.g., separating methane from higher hydrocarbons and NGLs. As such, the extraction units may separate one or more non-hydrocarbon compounds from one or more hydrocarbon compounds, or, when functioning as a de-methanizing unit, will separate at least one hydrocarbon component, i.e., methane, from at least one other hydrocarbon component, i.e., $C_2+$ compounds.

There are a number of different ways of chilling the gas to these temperatures, but one of the most effective is known as the turbo expander process. In this process, external refrigerants are used to cool the natural gas stream. Then, an expansion turbine is used to rapidly expand the chilled gases, which causes the temperature to drop significantly. This rapid temperature drop condenses ethane and other hydrocarbons in the gas stream, while maintaining methane in gaseous form. This process allows for the recovery of about 90 to 95 percent of the ethane originally in the gas stream. In addition, the expansion turbine is able to convert some of the energy released when the natural gas stream is expanded into recompressing the gaseous methane effluent, thus saving energy costs associated with extracting ethane.

The extraction of NGLs from the natural gas stream produces cleaner, purer natural gas, as well as enabling a more complete extraction of the valuable hydrocarbons that are the NGLs themselves.

B. Natural Gas Liquid Fractionation

Once higher hydrocarbons, e.g., ethane and NGLs have been removed from the natural gas stream, they are typically broken down into their base components that each has separate value. The process that is typically used to accomplish this task is called fractionation. Fractionation processes typically operate based on the different boiling points of the different hydrocarbons in the NGL stream. In some cases, fractionation is carried out in the same facility as the earlier gas processing steps, e.g., dehydration, de-acidification and extraction/de-methanization, while in other cases, fractionation occurs in a separate facility to which the composite NGLs are delivered.

In operation, fractionation occurs in stages where different hydrocarbons are boiled off, one by one, where the name of a particular fractionator alludes to its function, as it is conventionally named for the hydrocarbon that is boiled off. The entire fractionation process is broken down into steps, starting with the removal of the lighter NGLs from the stream. Accordingly, the process typically includes, in order, a de-ethanizer, which separates the ethane from the remaining NGL stream, a de-propanizer, which separates the propane from the remaining NGL stream, and a de-butanizer, which boils off the butanes. The remaining stream then primarily contains the pentanes and heavier hydrocarbons in the NGL stream. The separated butanes are also typically passed through a butane splitter or de-isobutanizer, which separates the iso and normal butanes. Thus, the fractionation system, whether referred to in its entirety or with respect to individual fractionation units, e.g., a de-propanizer, typically operates to separate at least one hydrocarbon component such as propane, from at least one other different hydrocarbon component, such as butane, pentane, etc. As will be appreciated, such separation may not be entirely complete. For example, the de-ethanizer may not remove 100% of the ethane from the remaining NGL stream. Likewise, subsequent individual fractionation units may not remove 100% of their respective compounds. In general, these fractionation steps will generally remove a substantial amount and majority of the compound for which they are targeted, from the remaining NGL stream, e.g., greater than 50%, greater than 60%, greater than 75% and even greater than 90% or 95%.

FIG. 1 provides a schematic illustration of major component processes and systems in a typical natural gas processing facility. As shown, raw gas from the gas well or other source 102, which may have been treated at the well or another intermediate processing unit or facility to remove water and other condensates, e.g., at step 104, is transported to an exemplary processing facility. Incoming raw gas 106 is then treated in an acid gas removal step/unit 108, to remove any hydrogen sulfide or other corrosive gases 110. The removed sulfur compounds or "acid gas" is subjected to additional processing, e.g., in sulfur unit 112, and additional processing to yield elemental sulfur and tail gases, which may be further processed and/or incinerated.

The de-acidified gas 114 is then passed through a dehydration unit 116 to remove further water, and then passed through one or more additional purification units 118, e.g., for removal of other impurities, such as mercury. The purified natural gas is then passed into an extraction unit 120, which may be a cryogenic extractor that comprises a cryogenic turbo expander unit 120a and a cryogenic nitrogen rejection unit 120b, for separation of methane in a methane rich stream 122a, and nitrogen 122b from the NGL stream 124. The resulting methane rich component is then passed on as pipeline ready natural gas, e.g., transferred to the sales gas pipeline for market, or as discussed in greater detail below, may be subjected to further processing. As noted above, extraction system 120 optionally may include a lean oil extraction unit in place of a cryogenic extraction unit.

The resulting demethanized NGL containing product 124, including ethane and other higher hydrocarbons (generally referred to herein as $C_2+$ components), is then passed through a fractionation train 126 that typically includes a de-ethanizer unit 128 that boils off the $C_2$ hydrocarbons 130 and passes the remaining fluids or "bottoms" 132 to a de-propanizer unit 134. The de-propanizer unit, in turn, boils off the $C_3$ gases 136, and passes the remaining bottoms 138 to a debutanizer unit 140, which boils off butanes 142, leaving pentanes and higher order hydrocarbons in stream 144. Each of the higher hydrocarbon streams 130, 136, 142 and 144, may then be subjected to additional processing, e.g., through sweetening units or butane splitters.

III. Steam Cracking

As noted above, other significant petrochemical processing revolves around the production of olefins and other higher hydrocarbons from natural gas, or petroleum distillates, like naphtha. In particular, saturated hydrocarbons may be processed or converted to unsaturated hydrocarbons through a process called steam cracking. In steam cracking, a gaseous or liquid hydrocarbon feed like naphtha, gas oil, liquefied petroleum gas ("LPG"), or ethane is diluted with steam and briefly heated in a furnace without the presence of oxygen. Typically, the reaction temperature is very high, at around 850° C. or higher, but the reaction is only allowed to take place very briefly. In modern cracking furnaces, the residence time is reduced to milliseconds to improve yield, resulting in gas velocities faster than the speed of sound. After the cracking temperature has been reached, the gas is quickly quenched to stop the reaction in a transfer line heat exchanger or inside a quenching header using quench oil. The resulting products are then further processed to separate distinct high value products, such as olefins, from undesirable by-products and unreacted feed gases.

As will be appreciated, many of the processes embodied in conventional steam cracker facilities share the same underlying principles of operation as those systems used in NGL processing or other processing facilities. For example, many of the separations systems, such as de-propanizer and/or de-ethanizer systems and C2 splitters, are typically included within cracker facilities to separate out unreacted components such as methane and ethane, or undesirable by-products from the olefin streams emanating from the cracker.

Figure 2:
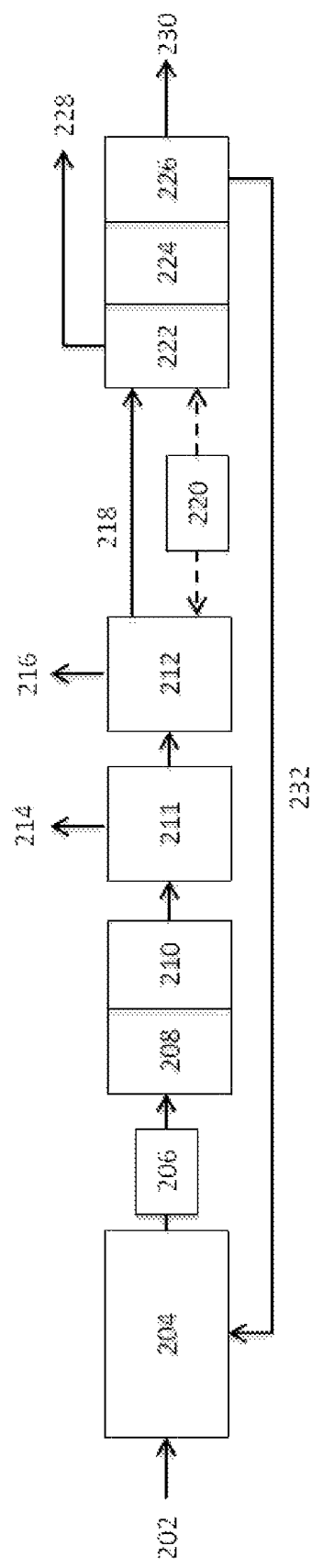
FIG. 2 presents a schematic illustration of major unit operations of an exemplary steam cracking facility.

FIG. 2 shows a schematic illustration of a steam cracker process and system. As shown, a feed gas stream 202, such as naphtha, or ethane from an NGL processing facility described above, is delivered along with a steam feed (not shown), to the cracker's furnace 204. Following cracking, the product is then quench cooled, e.g., in transfer line exchanger 206. The resultant product gas is then passed through compression and treatment steps (208 and 210), that may include, for example, multistage gas compression, with each stage followed by cooling and liquid hydrocarbon and water removal, as well as gas treating for removal of acid gas components, e.g., $H_2S$ and $CO_2$, as well as dehydration to remove water, before being transferred to the cryogenic section (cold-box) 211 for stagewise cooling and condensation of various components, in order to remove CO and hydrogen in output 214. The various liquid components are then fed to de-methanizer 212 to separate out C1 compounds 216, such as methane, from the higher hydrocarbons, e.g., C2+ compounds in stream 218. After de-methanizing, the C2+ rich stream 218 is then passed through further fractionation steps in e.g., de-ethanizer 222, to separate the C2 components from higher hydrocarbons in stream 228, an acetylene reactor 224, to convert acetylene in the C2 rich stream to ethylene and ethane, and C2 splitter 226 to separate ethylene from any residual ethane. The ethylene rich stream 230 is then recovered as product, while the residual ethane recovered from the C2 splitter is recycled back through the cracker furnace 204 in recycle stream 232.

IV. Integrated Catalytic Systems

In accordance with one embodiment the present invention, existing gas or petrochemical processing facilities or systems are integrated with novel processes and systems to yield a synergistic and highly valuable overall process. In particular, as provided herein, additional value-add catalytic reaction processes and reactor systems are integrated into conventional natural gas or other petrochemical processing facilities and systems to take in one or more outputs of these facilities and systems and/or provide one or more inputs into these facilities and systems, to leverage efficiency advantages derived from the combination of these processes over and above those processes individually. In particular, these integrated catalytic reactor systems will typically (1) take in one or more final or intermediate product streams from the processes performed in these facilities to catalytically convert those final or intermediate product streams into higher value or more easily managed materials, (2) contribute one or more of final or intermediate product streams to be further processed within one or more different processing units within these facilities, and/or (3) contribute and/or utilize thermal energy required by or produced by these processing systems.

The resulting integrated processing facilities have greatly enhanced efficiency and profitability, both in terms of the products produced as a function of the raw materials consumed, the types of feedstocks used, the types of products produced, and in terms of the energy requirements for operating those facilities. Consequently, the environmental impact of these facilities is substantially reduced, both in terms of reduced waste and reduced consumption of externally generated energy.

Of particular interest in the context of the invention, are integrated reactor systems for carrying out exothermic catalytic reactions used to convert natural gas constituents to higher value components, such as for converting methane and ethane to higher alkanes, olefins, and the like. Examples of such reactions include exothermic catalytic reactions for, e.g., the oxidative coupling of methane (OCM), as well as the oxidative dehydrogenation (ODH) of, e.g., methane, ethane, propane and other hydrocarbons.

With respect to one of these reactions, the oxidative coupling of methane ("OCM") to ethylene involves the following reaction: $2CH_4+O_2\rightarrow C_2H_4+2H_2O$, See, e.g., Zhang, Q., *Journal of Natural Gas Chem.*, 12:81, 2003; Olah, G. "Hydrocarbon Chemistry", Ed. 2, John Wiley & Sons (2003). This reaction is exothermic ($\Delta H=-67$ kcals/mole) and has typically been shown to occur at very high temperatures (>700° C.). Although the detailed reaction mechanism is not fully characterized, experimental evidence suggests that free radical chemistry is involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couple in the gas phase to form ethane ($C_2H_6$), followed by dehydrogenation to ethylene ($C_2H_4$). Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction under practical operating conditions. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e. ethane and ethylene), and more importantly, all such reported yields operate at extremely high temperatures (>800 C).

Although primarily described in terms of integrating an OCM reactor system it will be appreciated that additional reactor systems may likewise be integrated, such as ODH reactor systems. Oxidative dehydrogenation (ODH) of light alkanes offers an attractive route to alkenes, since, like the OCM reaction, the reaction is exothermic and avoids the thermodynamic constraints of non-oxidative routes by forming water as a byproduct. In addition, carbon deposition during ODH is eliminated, leading to stable catalytic activity. However, the yield of alkenes obtained by ODH on most catalysts is limited by alkene combustion to CO and $CO_2$ ($CO_x$). ODH reactor systems and associated catalysts have been described in the art.

In one aspect, the present invention provides modular OCM reactor systems that are configured to "plug in" to, and in preferred aspects are integrated into existing natural gas processing facilities. As used herein, a natural gas processing facility refers to a facility that takes in one or more of natural gas or NGLs, and produces more than one product from these inputs. As such, a gas processing plant may take in natural gas and produce pipeline ready natural gas as well as NGLs, or it may take in NGLs and fractionate them to produce two or more different NGL products therefrom. As will be appreciated, the specific configuration and type of processing plant will depend upon the material taken in and the products produced therefrom, and would encompass in many cases, for example, NGL extraction plants, fractionators, straddle plants, and the like, that meet the aforementioned criteria.

In certain aspects, the processing facilities that are the subject of the invention will include one or more of an extraction unit and a fractionation unit, and optionally one or more additional processing units, with a minimum of customized retrofitting to such facilities. Further, the integrated OCM reactor systems in the context of the invention are integrated and configured to take up one or more effluent streams from different processing units within these facilities as a feed stream to the OCM reactor system, contribute one or more effluent streams to one or more different processing units within these facilities as a feed stream to those units, utilize thermal energy produced elsewhere in the facility to carry out the OCM reaction, and/or contribute thermal energy to other systems and processing units elsewhere in the facility.

As used herein, an OCM reactor system typically includes one or more reactor vessels that contain an appropriate OCM catalyst material, typically in conjunction with additional system components. A variety of OCM catalysts have been described previously. See, e.g., U.S. Pat. Nos. 5,712,217, 6,403,523, and 6,576,803. While these catalysts have been shown to catalyze an OCM reaction, for most of these catalysts, the reactions are carried out under conditions that are less practical or economical, i.e., at very high temperatures and/or pressures. Recently, novel catalysts have been discovered that yield conversion and selectivity that enable economic methane conversion at practical operating conditions. These are described in, for example, Published U.S. Patent Application No. 2012-0041246, as well as patent application Ser. Nos. 13/479,767, filed May 24, 2012, and 61/651,399, filed May 24, 2012, the full disclosures of each of which are incorporated herein by reference in their entirety for all purposes.

Products produced from these catalytic reactions typically include CO, $CO_2$, $H_2O$, $C_2$+ hydrocarbons, such as ethylene, ethane, and larger alkanes and alkenes. In preferred aspects, the OCM reactor systems operate to convert methane, e.g., the methane component of natural gas, into desired higher hydrocarbon products (ethane, ethylene, propane, propylene, butanes, pentanes, etc.) collectively referred to as $C_2$+ compounds with high yield. In particular, the progress of the OCM reaction is generally discussed in terms of methane conversion, $C_2$+ selectivity, and $C_2$+ yield. As used herein, methane conversion generally refers to the percentage or fraction of methane introduced into the reaction that is converted to a product other than methane. $C_2$+ selectivity generally refers to the percentage of all carbon containing products of the OCM reaction that are the desired $C_2$+ products, e.g., ethane, ethylene, propane, propylene, etc. Although primarily stated as $C_2$+ selectivity, it will be appreciated that selectivity may be stated in terms of any of the desired products, e.g., just $C_2$, or just $C_2$ and $C_3$. Finally, $C_2$+ yield generally refers to the amount of carbon that is incorporated into a $C_2$+ product as a percentage of the amount of carbon introduced into a reactor in the form of methane. This may generally be calculated as the product of the conversion and the selectivity divided by the number of carbon atoms in the desired product. $C_2$+ yield is typically additive of the yield of the different $C_2$+ components included in the $C_2$+ components identified, e.g., ethane yield+ethylene yield+propane yield+propylene yield etc.)

Preferred OCM reactor systems typically provide a methane conversion of at least 10% per process pass in a single integrated reactor system (e.g., single isothermal reactor system or integrated multistage adiabatic reactor system), with a $C_2$+ selectivity of at least 50%, but at reactor inlet temperatures of between 400 and 600° C. and at reactor inlet pressures of between about 15 psig and about 150 psig. In preferred aspects, the single pass conversion will be 10% or greater with a selectivity of 60% or greater, and in more preferred aspects, a conversion of 15% or greater, with a selectivity of 50% or greater, or even a selectivity of 60% or greater. Likewise, in preferred aspects, the reactor inlet pressures will be between about 15 and about 135 psig, more preferably, less than about 120 psig, less than about 100 psig, less than about 90 psig, less than about 85 psig, or less than about 80 psig, or even less than about 70 psig. In some cases, the reactor inlet pressure may be between about 30 and about 100 psig, or even between about 30 and about 90, or 85, or 80 psig, while achieving the preferred selectivities and conversions, described above. Thus, the catalysts employed within these reactor systems are capable of providing the described conversion and selectivity under the described reactor conditions of temperature and pressure. In the context of preferred OCM catalysts and systems, it will be appreciated that the reactor inlet or feed temperatures typically substantially correspond to the minimum "light-off" or reaction initiation for the catalyst or system. Restated, the feed gases are contacted with the catalyst at a temperature at which the OCM reaction is able to be initiated upon introduction to the reactor. Because the OCM reaction is exothermic, once light-off is achieved, the heat of the reaction would be expected to maintain the reaction at suitable catalytic temperatures, and even generate excess heat, as described elsewhere herein.

In particularly preferred aspects, the OCM reactors and reactor systems, when carrying out the OCM reaction, operate at pressures of between about 15 psig and about 125 psig at the above described temperatures, while providing the conversion and selectivity described above, and in more preferred aspects, at pressures less than 100 psig, e.g., between about 15 psig and about 100 psig, or even less than about 90 psig.

Examples of particularly useful catalyst materials are described in, for example, Published U.S. Patent Application No. 2012-0041246, as well as patent application Ser. Nos. 13/479,767, filed May 24, 2012, and 61/651,399, filed May 24, 2012, previously incorporated herein by reference in their entirety for all purposes. The catalysts may comprise bulk catalyst materials, e.g., having relatively undefined morphology or, in certain preferred aspects, the catalyst material comprises, at least in part, nanowire containing catalytic materials. In some cases, the nanowire catalysts have an aspect ratio that is greater than about ten. In either form, the catalysts used in accordance with the present invention may be specifically employed under the full range of reaction conditions described above, or in any narrower described range of conditions. Similarly, the catalyst materials may be provided in a range of different larger scale forms and formulations, e.g., as mixtures of materials having different catalytic activities, mixtures of catalysts and relatively inert or diluent materials, incorporated into extrudates, pellets, or monolithic forms, or the like. Ranges of exemplary catalyst forms and formulations are described in, for example, U.S. Patent Application No. 61/651,396, filed May 24, 2012, the full disclosure of which is incorporated herein by reference in its entirety for all purposes.

The reactor vessels used for carrying out the OCM reaction in the OCM reactor systems of the invention may include one or more discrete reactor vessels each containing OCM catalyst material, fluidly coupled to a methane source and a source of oxidant as further discussed elsewhere herein. Feed gas containing methane is contacted with the catalyst material under conditions suitable for initiation and progression of the reaction within the reactor to catalyze the conversion of methane to ethylene and other products.

For example, the OCM reactor system may comprise one or more staged reactor vessels operating under isothermal or adiabatic conditions, for carrying out OCM reactions. For adiabatic reactor systems, the reactor systems may include one, two, three, four, five or more staged reactor vessels arranged in series, which are fluidly connected such that the effluent or "product gas" of one reactor is directed, at least in part, to the inlet of a subsequent reactor. Such staged serial reactors provide higher yield for the overall process, by allowing catalytic conversion of previously unreacted methane. These adiabatic reactors are generally characterized by the lack of an integrated thermal control system used to maintain little or no temperature gradient across the reactor. With no integrated temperature control system, the exothermic nature of the OCM reaction results in a temperature gradient across the reactor indicative of the progress of the reaction, where the inlet temperature can range from about 400° C. to about 600° C., while the outlet temperature ranges from about 700° C. to about 900° C. Typically, such temperature gradients can range from about 100° C. to about 500° C. By staging adiabatic reactors, with interstage cooling systems, one can step through a more complete catalytic reaction without generating extreme temperatures, e.g., in excess of 900° C.

In operation, methane-containing feed gas is introduced into the inlet side of a reactor vessel, e.g., the first reactor in a staged reactor system. Within this reactor, the methane is converted into $C_2+$ hydrocarbons, as well as other products, as discussed above At least a portion of the product gas stream is then cooled to an appropriate temperature and introduced into a subsequent reactor stage for continuation of the catalytic reaction. In particular, the effluent from a preceding reactor, which in some cases may include unreacted methane, can provide at least a portion of the methane source for a subsequent reactor. An oxidant source and a methane source, separate from the unreacted methane from the first reactor stage, are also typically coupled to the inlet of each subsequent reactor.

In alternative aspects, the reactor systems may include one or more 'isothermal' reactors, that maintain a relatively low temperature gradient across the length or depth of the overall reactor bed, e.g., between the inlet gas and outlet or product gas, through the inclusion of integrated temperature control elements, such as coolant systems that contact heat exchange surfaces on the reactor to remove excess heat, and maintain a flat or insignificant temperature gradient between the inlet and outlet of the reactor. Typically, such reactors utilize molten salt or other coolant systems that operate at temperatures below 593 C. As with adiabatic systems, isothermal reactor systems may include one, two, three, ten or more reactors that may be configured in serial or parallel orientation. Reactor systems for carrying out these catalytic reactions are also described in U.S. Patent Application No. 61/651,485, filed May 24, 2012, the full disclosure of which is incorporated herein by reference in its entirety for all purposes.

The OCM reactor systems used in the present invention also typically include thermal control systems that are configured to maintain a desired thermal or temperature profile across the overall reactor system, or individual reactor vessels. In the context of adiabatic rector systems, it will be appreciated that the thermal control systems include, for example, heat exchangers disposed upstream, downstream or between serial reactors within the overall system in order to maintain the desired temperature profile across the one or more reactors. In the context of reactors carrying out exothermic reactions, like OCM, such thermal control systems also optionally include control systems for modulating flow of reactants, e.g., methane containing feed gases and oxidant, into the reactor vessels in response to temperature information feedback, in order to modulate the reactions to achieve the thermal profiles of the reactors within the desired temperature ranges. These systems are also described in co-pending U.S. Patent Application No. 61/651,485, previously incorporated herein by reference.

For isothermal reactors, such thermal control systems include the foregoing, as well as integrated heat exchange components, such as integrated heat exchangers built into the reactors, such as tube/shell reactor/heat exchangers, where a void space is provided surrounding a reactor vessel or through which one or more reactor vessels or tubes pass. A heat exchange medium is then passed through the void to remove heat from the individual reactor tubes. The heat exchange medium is then routed to an external heat exchanger to cool the medium prior to recirculation into the reactor.

In certain preferred aspects, the products of the OCM reactor systems integrated into processing facilities are transferred to additional process components for production of higher hydrocarbons, e.g., $C_3+$ hydrocarbons from the products of the OCM reaction. In particular, $C_2+$ hydrocarbons derived from the OCM reaction process, and which optionally include the extraction processes described above or are upstream of such extraction processes, are subjected to additional processing for conversion of the $C_2+$ hydrocarbons, like ethylene, into even higher hydrocarbons, like $C_3+$ hydrocarbons, NGLs, cyclic hydrocarbons, linear and branched alkanes, aromatics, and the like. As will be appreciated, although generally phrased in terms of the effluent from the OCM reactor system, it will be appreciated that effluent from individual reactor stages may be routed to follow on process steps, including, e.g., demethanization, where separated $C_2+$ compounds are routed to a different process, while the methane rich streams are passed through subsequent reactor stages. As a result, efficiencies in processing and reaction equilibria may be favorably skewed over multiple stages.

For ease of discussion, these additional processes are generally referred to herein as 'oligomerization' processes, although this term encompasses a range of different reaction types. Likewise, the processing units or systems for carrying out these reactions are generally referred to herein as "oligomerization systems" or "units", although such terminology includes a range of different reactions for conversion of higher hydrocarbons from $C_2$ hydrocarbons, e.g., ethane and ethylene. Examples of such reactions include, for example; targeted oligomerization of ethylene optionally followed by hydrogenation to form narrow distributions of linear or branched alkanes such as butanes, hexanes, octanes, decanes, dodecanes, tetradecanes, etc, non-targeted oligomerization of ethylene optionally followed by hydrogenation to form broad distributions of linear or branched alkanes such as hydrocarbons within the $C_4$-$C_{16}$+ range, dimerization of ethylene to butenes followed by dimerization to i-octanes, non-targeted oligomerization of ethylene optionally followed by hydrogenation to form a mixture of aromatics, alkanes, alkenes, that is nominally a gasoline blendstock, non-targeted oligomerization of ethylene optionally followed by hydrogenation to form a mixture of branched, non-branched, and cyclic alkanes that is nominally a diesel or jet fuel blendstock, non-targeted oligomerization of ethylene to form narrow distributions of aromatics, such as benzene, toluene and xylenes (collectively, "BTX"), or benzene, toluene, ethyl-benzene, xylene ("BTEX"), for use as a chemical feedstock. In general, many of these oligomerization processes involve catalytic reactions and reactor systems for conversion of $C_2$+ hydrocarbons to larger hydrocarbons. The nature and configuration of the oligomerization reactor and catalyst system will depend upon the specific type of product desired. In preferred embodiments the oligomerization reaction takes place over a heterogeneous catalyst in a fixed bed reactor (either adiabatic or isothermal) although there are methods and processes for homogeneous catalysts known to one skilled in the art as well, and these can be used in combination such as a heterogeneous process for dimerization of ethylene to butenes and homogeneous process for butenes to octenes. A variety of these further conversion processes that may be integrated into the processes described herein, are described in, e.g., U.S. Provisional Patent Application No. 61/734,865, filed Dec. 7, 2012, the full disclosure of which is hereby incorporated herein by reference in its entirety for all purposes.

As will be appreciated, the outputs of the additional processes, e.g., oligomerization processes, may likewise be routed through the integrated unit operations of a gas processing facility, cracker facility or other processing facility, in accordance with the invention. For example, separation processes may be equally applicable to the oligomerization products as they are to OCM products and cracking products. Further, oligomerization products may be routed into upstream unit processes, including the cracker itself, for back-cracking of LAOs or other higher hydrocarbons to form more diverse products.

For ease of discussion, in addition to one or more reactor vessels and associated piping and conduits, the phrase OCM reactor system also typically includes those elements that allow ready integration of an OCM process into an existing gas processing path or plant. As such, such OCM reactor systems may include heat exchangers for both elevating the temperature of feed gases to reach appropriate temperatures for catalysis, as well as cool product gases to meet temperature requirements of subsequent process steps. Similarly, such reactor systems may include compressors, pumps and the like, for applying appropriate pressures for delivering feed gases or recycle streams into the reactor systems and/or product streams to other processing units, e.g., separation or fractionation units.

V. OCM Gas Processing Integration

A. Generally

OCM reactor systems and processes may be integrated into existing natural gas or other petrochemical processing facilities in one or more of a number of different specific points in such facilities, and with respect to a number of different inputs and outputs of either or both the OCM system and the unit processes of the overall processing facility. Examples of such OCM reactor systems and processes are described in U.S. Provisional App. No. 61/669,523, filed Jul. 9, 2012, the full disclosure of which is hereby incorporated by reference in its entirety for all purposes. In particular, the OCM reactor systems of the invention may be integrated into conventional processing plants as one or both of a producer of feed streams for one or more processing units within the processing facility, and/or as a consumer of product streams from one or more processing units within the processing facility.

In the context of the present invention, integration includes a range of different integration types, including, e.g., process integration through fluid or gas coupling within a process stream. Fluid integration or fluid coupling or connection generally refers to a persistent fluid connection or fluid coupling between two systems within an overall system or facility. Such persistent fluid communication typically refers to an interconnected pipeline network coupling one system to another. Such interconnected pipelines may also include additional elements between two systems, such as control elements, e.g., heat exchangers, pumps, valves, compressors, turbo-expanders, sensors, as well as other fluid or gas transport and/or storage systems, e.g., piping, manifolds, storage vessels, and the like, but are generally entirely closed systems, as distinguished from two systems where materials are conveyed from one to another through any non-integrated component, e.g., railcar or truck transport, or systems not co-located in the same facility or immediately adjacent facilities. As used herein, fluid connection and/or fluid coupling includes complete fluid coupling, e.g., where all effluent from a given point such as an outlet of a reactor, is directed to the inlet of another unit with which the reactor is fluidly connected. Also included within such fluid connections or couplings are partial connections, e.g., were only a portion of the effluent from a given first unit is routed to a fluidly connected second unit. Further, although stated in terms of fluid connections, it will be appreciated that such connections include connections for conveying either or both of liquids and gas.

In other aspects, integration refers to thermal or energy integration of, e.g., an OCM reactor system, into the energy infrastructure of a facility. Such integration may also include spatial integration of en OCM reactor system into the physical processing plant, e.g., "inside battery limits" (IBL), or it may be otherwise integrated, but outside battery limits (OBL) of the facility.

Figure 3:
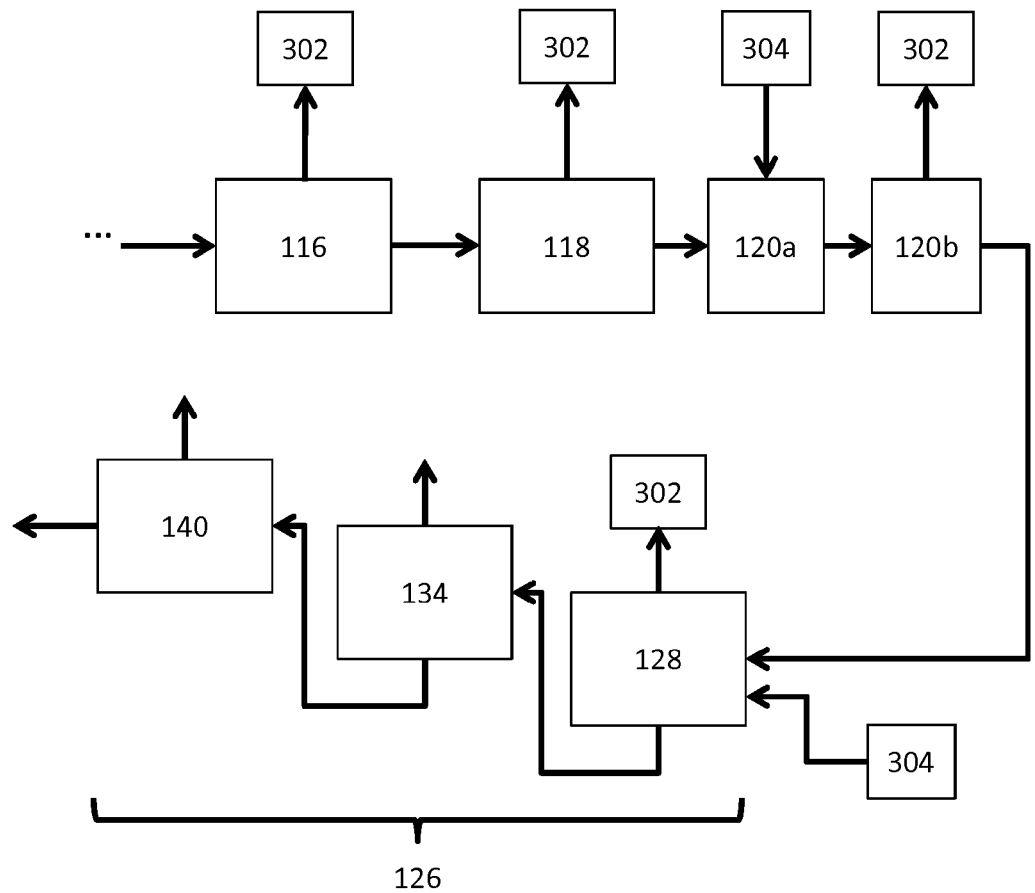
FIG. 3 presents a block diagram showing potential points where inputs and outputs of an OCM reactor system would integrate into a conventional natural gas processing system or facility.

FIG. 3 schematically illustrates a number of potential integration points for an OCM reactor system in the overall process path of a natural gas processing facility shown in FIG. 1. In particular, as shown, an OCM input, schematically identified as block 302, is shown integrated into and fluidly coupled at multiple points in the process stream, where the output or product of a particular processing unit is fed into the inlet of an OCM reactor system. For example, as shown, the OCM reactor is shown optionally fluidly coupled to the output of, e.g., dehydration unit 116 or purification unit 118, extraction unit 120b, and de-ethanizer unit 128.

Alternatively or additionally, the OCM reactor output, schematically illustrated as block 304, is shown integrated, e.g., fluidly connected, with multiple points in the process stream where the OCM reactor product streams are fed into various processing units of the overall facility. By way of example, the OCM output 304, may optionally be fluidly coupled to the inlet of the extraction unit 120, fractionation train 126, e.g., fractionation units 128, 134 or 140, or further processing units (not shown).

1. OCM Feed

In one embodiment, an OCM reactor system is connected downstream of one or more processing units in a gas processing facility whereby product streams from the processing unit are fed into the inlet stream of the OCM reactor system. In particular, processing units that include as one or more outputs, methane containing, and preferably methane rich streams, can provide feed gases to the OCM reactor system, for conversion of methane to higher hydrocarbons. Likewise, the outputs of the OCM system can generally provide feed streams to, and leverage the infrastructure of a number of systems in conventional processing units used to separate, modify and purify hydrocarbon mixtures.

In a first simple example, an OCM reactor system is provided integrated into an existing processing facility to take up at least a portion of the clean, dry pipeline ready natural gas for conversion of the methane contained in that gas, into higher hydrocarbons, instead of passing that portion of the dry gas through the extraction and fractionation units. In this context, the inlet to the OCM reactor system may be fluidly coupled to the outlet of the acid gas removal unit 108, dehydration unit 116, or, as shown, additional purification unit 118. As noted, this fluid connection may include one or more heat exchangers, pumps, compressors, or the like to present the dry gas to the OCM reactor system under conditions appropriate for initiation of the OCM catalytic reaction, e.g., inlet temperatures between 450° C. and 600° C., and pressures of 1 atm or greater, and preferably, from about 15 psig to about 150 psig, 15 psig to about 125 psig, or less than 100 psig, or from about 15 psig to about 100 psig.

Alternatively or additionally, the OCM reactor system is fluidly coupled to one or more outlets of the extraction unit(s) 120, to route methane rich effluents from the extraction unit 120 into the OCM reactor system for conversion of methane to ethylene and other hydrocarbons, which, as discussed in greater detail below, again may be passed through the extraction unit to separate ethylene and other C2+ components from gas components, e.g., CO, $CO_2$, $N_2$ and unreacted methane. In accordance with the invention, these and other outputs of conventional processing facilities are beneficially exploited. For example, in some cases, $CO_2$ recovered from the OCM reactor products and separated in the extraction unit may be transported via pipeline or truck, used onsite, or otherwise beneficially used in enhanced oil recovery (EOR). Likewise, $N_2$ from the OCM reactor product and separated in the extraction unit is optionally recovered, and transported via pipeline or truck, used onsite, or otherwise beneficially used in, e.g., enhanced oil recovery (EOR). Similarly, $H_2O$ from the OCM reactor product that is separated in the OCM extraction or other purification units may be recovered and transported via pipeline or truck, used onsite, or otherwise beneficially used, e.g., as a fracking fluid.

Optionally, or in addition to the foregoing, ethane rich streams from the fractionation train 126, e.g., ethane rich effluent from de-ethanizer unit 128, that may include small amounts of methane not previously removed, may be cycled into the OCM reactor, either alone, or in combination with one or more methane rich streams, to convert any residual methane in the OCM reactor to higher hydrocarbons. Further, as an intermediate in the OCM process, under the same reaction conditions of OCM, ethane present in the OCM feed may be reacted and converted into ethylene in the OCM reactor.

Ethane rich streams from the de-ethanizer may likewise be routed to ethane conversion systems. Such ethane conversion systems include, for example, steam cracking units that convert ethane to ethylene via non-oxidative dehydrogenation. Alternatively, the ethane may be routed to additional reactor systems containing catalysts for oxidative dehydrogenation ("ODH") of ethane in the presence of an oxygen source, to produce ethylene. Catalysts and systems for carrying out ODH reactions are described in, for example, Cavani, et al., Catalysis Today (2007), Vol. 127 (1-4), 113-131, the full disclosure of which is incorporated herein by reference in its entirety for all purposes. Again, the outlet streams of either of these systems may be additionally recycled or routed as needed to other processing units within the facility.

2. OCM Product

In another embodiment, and as noted above, the OCM reactor system is provided upstream of one or more processing units in the gas processing facility, so that product streams from the OCM reactor system, referred to as "OCM product streams" or "OCM product gases", may be further processed by different processing units within the facility.

For example, an OCM reactor system product stream, that typically includes C2+ hydrocarbons, as well as potentially CO, $CO_2$, $N_2$ and unreacted methane and other products, is passed through the extraction unit 120, such as a two stage cryogenic extraction unit 120a and 120b, to separate the ethylene, ethane, and other C3 through C5+ hydrocarbons, from the nitrogen, CO and $CO_2$ components, as well as any residual methane and other gas components. An example of a cryogenic extraction system for processing OCM product streams is described in co-pending U.S. Patent Application No. 61/586,711, filed Jan. 13, 2012, which is incorporated herein by reference in its entirety for all purposes. Briefly, exemplary cryogenic extraction systems typically include at least first and second separation units (e.g., separations units 120a and 120b), where the first unit (120a) reduces the temperature of the incoming gas, e.g., NGL containing natural gas, or an OCM product gas. For purposes of discussion, the separations system is described in terms of an OCM Product gas. The first separations unit within a cryogenic separations system typically functions as a de-methanizer, as the reduction in temperature liquefies the $C_2$+ components to result in a bottoms portion that is $C_2$+ rich, while the remaining gas component, comprising mainly methane and $N_2$ components are removed from the top of the unit. This methane containing component is then passed through the second separations unit (120b) which functions as a nitrogen rejection unit by liquefying the methane component and venting the nitrogen component.

Similarly, the OCM reactor system could also be provided fluidly coupled to a lean oil extraction unit for separation of the lighter hydrocarbon components from the other gas components.

In an alternative or additional example, a product stream from the OCM reactor system, or optional oligomerization system, is optionally routed through the fractionation system, or one or more individual fractionation units of a conventional gas processing facility, to separate heavier hydrocarbons, e.g., $C_3$, $C_4$ or $C_5+$ hydrocarbons and NGLs, from the lighter hydrocarbons, e.g., ethane and ethylene. In such processes, the ethane may be pulled as a product or as noted elsewhere herein, redirected back into the OCM reactor system or to an ethane conversion process, e.g., as described above. As will be appreciated, the OCM product may be routed through a full length fractionation system, e.g., multiple staged fractionation units, or may be routed through any individual or any subset of fractionation units in the overall fractionation system, e.g., just a de-ethanizer, or just a de-ethanizer and/or depropanizer, etc.

As will be appreciated, the integration of the OCM reactor system in an upstream or downstream configuration as to one or more processing units within a gas processing facility, is not mutually exclusive, as in many cases, the OCM reactor will take inputs from and provide outputs to multiple different processing units in the processing facility, and in some cases will take inputs from and provide outputs to a single processing unit, e.g., a cryogenic extraction unit or a fractionation unit.

Figure 4:
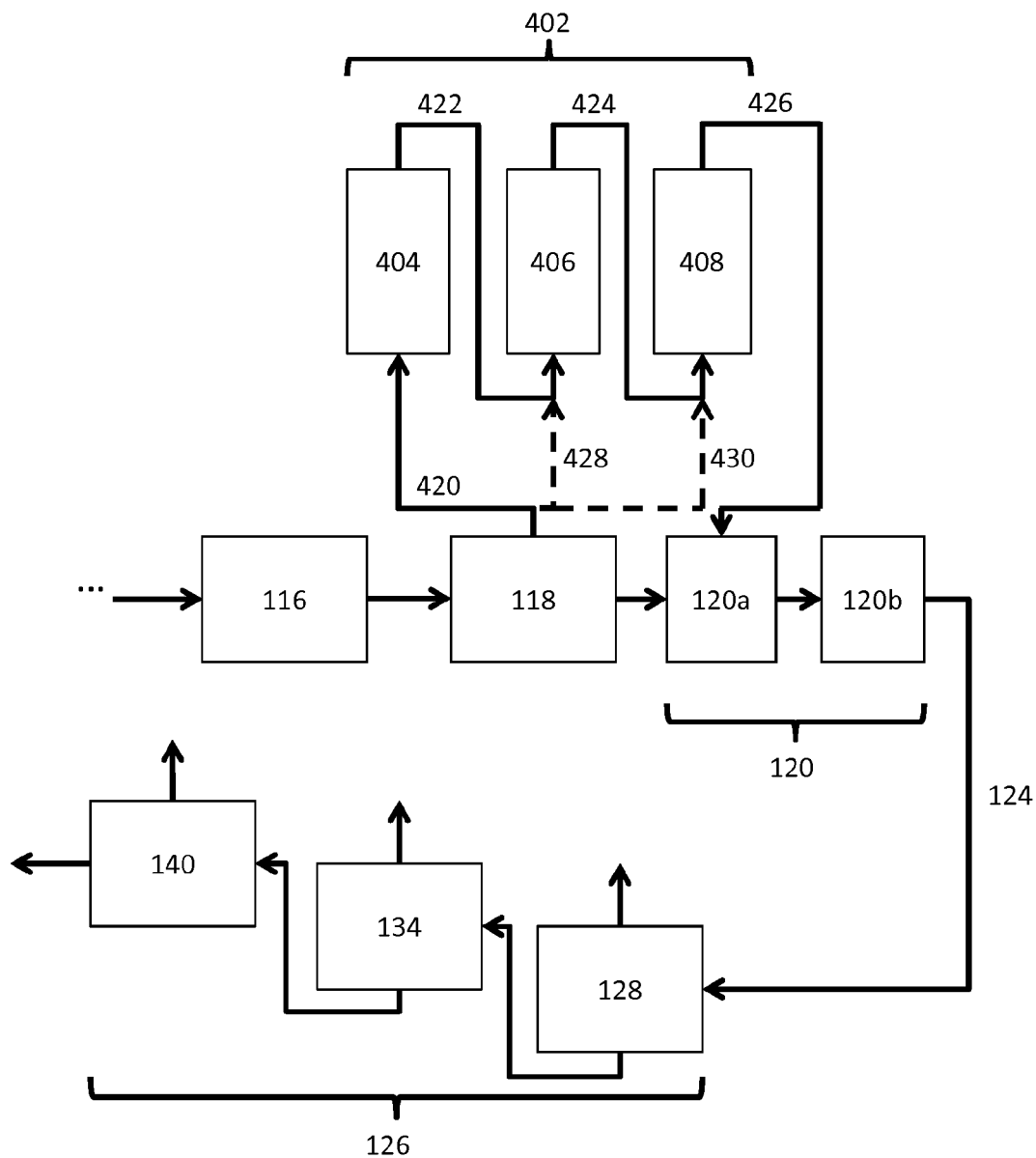
FIG. 4 presents a schematic illustration of an adiabatic OCM reactor system integrated into a first location in a natural gas processing facility.

FIG. 4 schematically illustrates one example of an OCM reactor system integrated into a conventional gas processing facility. In particular, shown is a staged adiabatic OCM reactor system 402 coupled to the outlet of the purification unit 118 of a gas facility. As shown, a clean, dry gas stream 420 from purification unit 118, which may be a portion or all of the output of the purification unit 118 at a particular time, is routed to the inlet of first reactor 404 of a staged adiabatic OCM reactor system 402. The product stream 422 from reactor 404 is then, at least partially, introduced into the inlet of reactor 406, whose product stream 424, is at least partially introduced into the inlet of reactor 408. While illustrated as a three-stage adiabatic reactor system 402, it will be appreciated that two three, four or more stages may be employed in an adiabatic system. Such staged adiabatic systems are described in co-pending U.S. Provisional Patent Application No. 61/651,485, filed May 24, 2012, and incorporated herein by reference in its entirety for all purposes.

As shown, additional clean dry gas from purification unit 118 may also be introduced into the subsequent reactors 406 and 408 in addition to the product stream of the preceding reactor, e.g., product streams 422 and 424, respectively, as shown by dashed arrows 428 and 430, to provide an additional source of methane for these subsequent reactors.

In addition to taking up at least a portion of the product stream from the purification unit(s) 118 of the facility, the OCM product stream of the overall OCM reactor system, e.g., shown as the effluent stream 426 from reactor 408, may also be subjected to subsequent processing in the further processing units of the gas processing facility.

In particular, as shown in FIG. 4, the outlet of the OCM reactor system 402 is fluidly coupled to the inlet of the extraction unit 120 such that OCM product stream 426 is introduced into the extraction unit 120, to separate higher hydrocarbons, e.g., $C_2+$ components, in stream 124, from any residual methane and nitrogen within the OCM product gas stream 426, e.g., in the cryogenic demethanizing unit 120a. These higher hydrocarbons are then optionally routed to the fractionation train 126, e.g., units 128, 134 and 140, for separation of the various different $C_2+$ constituents from the de-methanized product stream 124. The fractionation unit is also referred to herein as a $C_2+$ fractionation unit. The methane and nitrogen containing components are then optionally routed through the nitrogen rejection unit, e.g., unit 120b, to separate the nitrogen from the methane, which methane optionally may then be re-introduced into the OCM reactor system 402 (not shown). As noted above, the cryogenic demethanizing unit, the entire cryogenic system 120, or a similar separations unit may be positioned to receive the effluent gas from individual reactor stages, e.g., stages 404 and 406, as opposed to just receiving the final OCM reactor system product gas (stream 426), in order to skim off C2+ compounds from streams 422 and 424, respectively, while passing methane into the subsequent reactor stages for conversion. The resulting C2+ containing streams would then be routed for subsequent processing, e.g., in fractionation train 126. As noted, this would allow efficiencies in terms of reducing $C_2+$ product losses from stage to stage, as well as improving efficiencies of reactions based upon shifting equilibria, e.g., higher relative reactant concentration in each of the subsequent stages.

Figure 5:
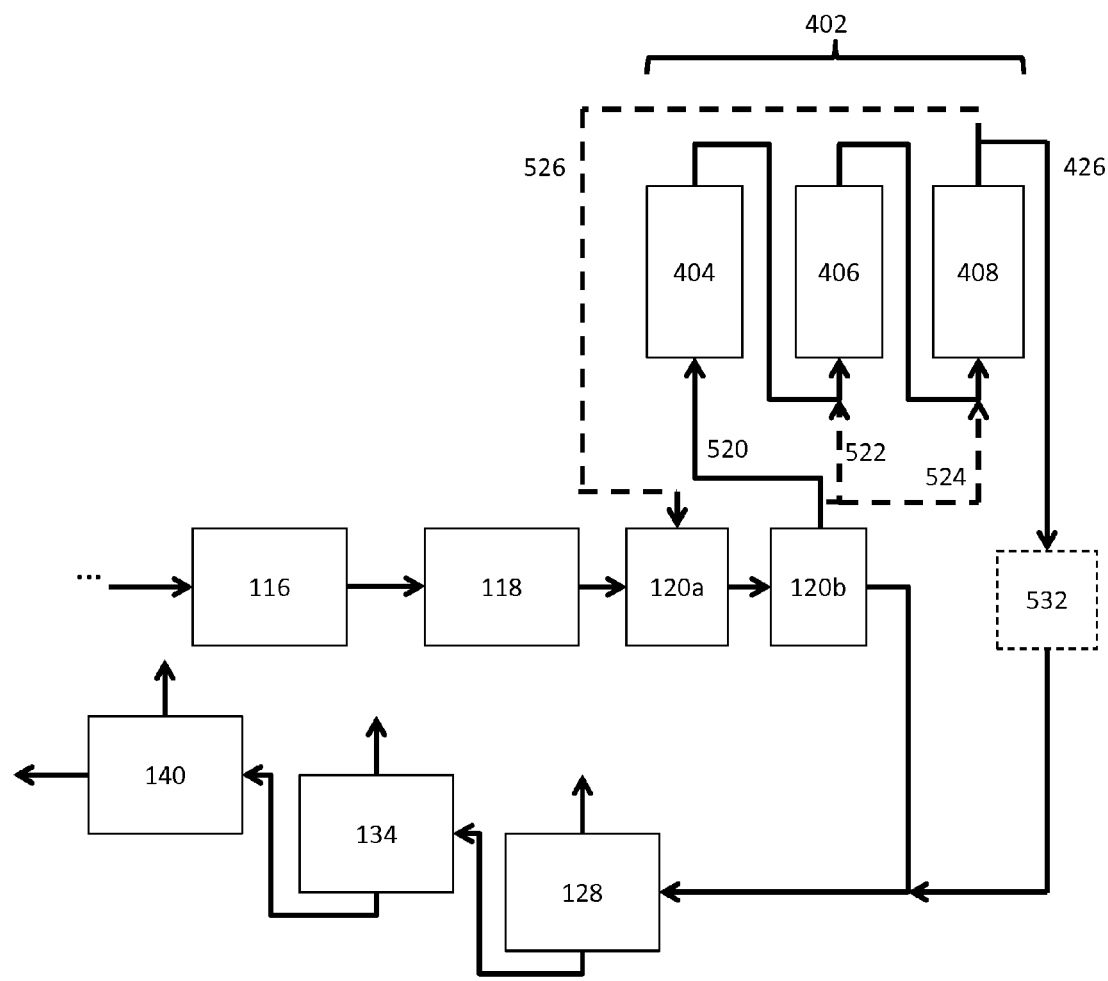
FIG. 5 provides a schematic illustration of an adiabatic OCM reactor system integrated into a second location in a natural gas processing facility.

FIG. 5 schematically illustrates coupling of the OCM reactor system 402 with the extraction unit 120, and particularly, the cryogenic separation unit 120b and the fractionation system, e.g., through de-ethanizer 128. In particular, as shown, the methane rich gas effluent stream 520 from the cryogenic extraction unit 120b is introduced as a feed gas into the inlet of reactor 404. As noted above, the product gas from the first staged reactor is, at least partially, fed into the subsequent reactors 406 and 408, along with optional additional methane containing gas feeds 522 and 524 from the outlet of cryogenic extraction unit 120b. The product gas stream 426 from the OCM reactor system 402 is then fed into the fractionation train 126 in order to separate out the various constituent $C_2+$ products. As shown, the OCM is optionally passed through optional oligomerization unit 532, for conversion of $C_2+$ hydrocarbons, e.g., ethylene, to higher hydrocarbons, e.g., $C_3+$ hydrocarbons, which are then transferred to the fractionation system for separation of different higher hydrocarbons. Optionally the output of the oligomerization unit 532 can be transferred to the fractionation system at various points, including but not limited to the input or output of units 128, 134, 140.

Alternatively, or additionally, the product stream from the OCM reactor system is fed back through the extraction units 120, as shown by the dashed line 526 from the outlet of reactor 408, in order to separate any residual methane and/or nitrogen from the desired OCM products, e.g., $C_2+$ products, as described above.

Alternatively, or additionally, the product stream from the oligomerization system is fed back through the extraction units 120, in order to separate any residual methane and/or nitrogen from the desired oligomerization products, e.g., $C_2+$ products, as described above.

VI. OCM-Cracker Integration

Figure 6:
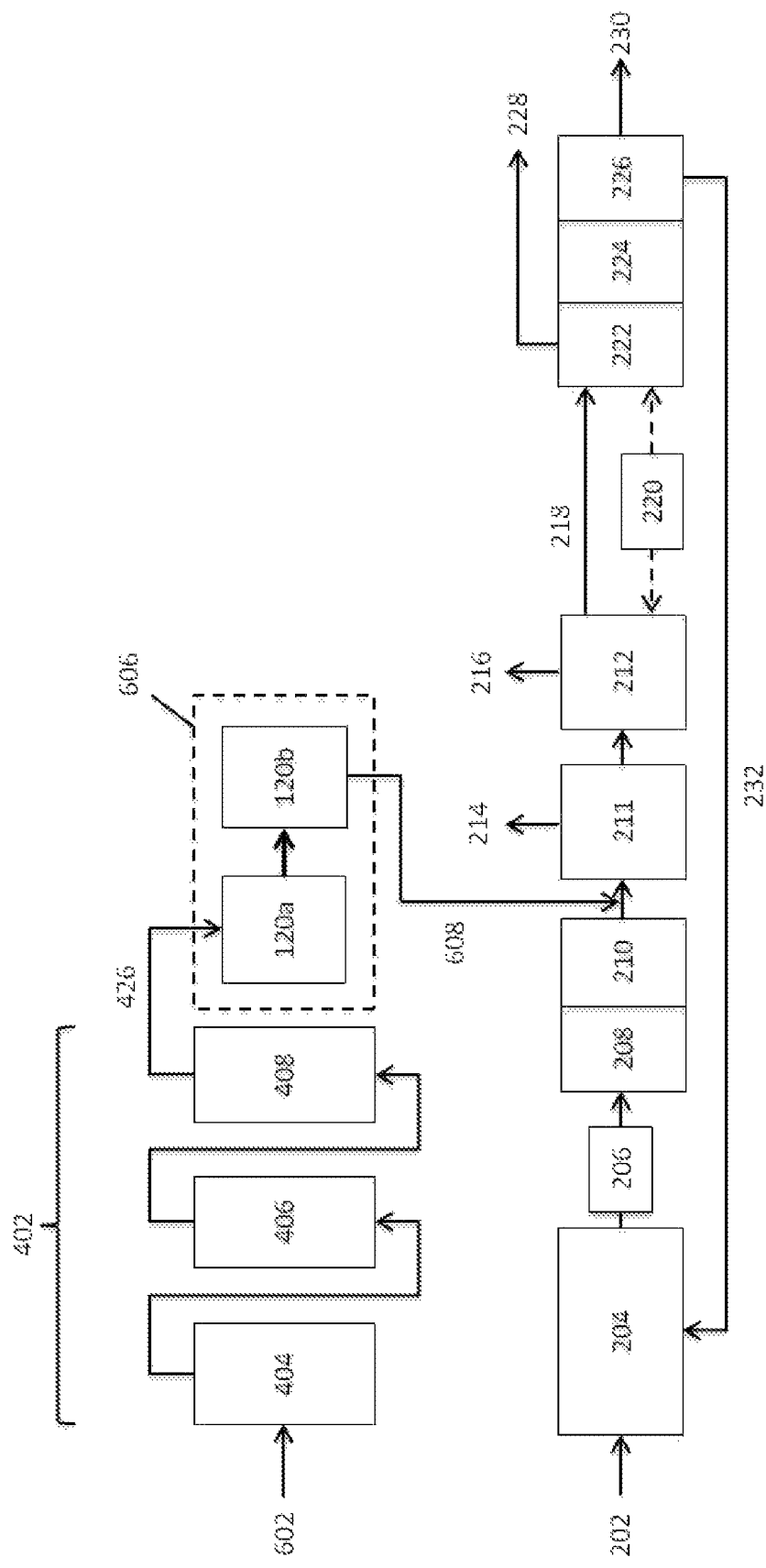
FIG. 6 provides a schematic illustration of an adiabatic OCM reactor system and cryogenic separation system integrated into an exemplary steam cracking facility.

As with natural gas processing facilities described above, substantial value is derived from integration of OCM reactor systems into existing cracker facilities, such as ethane or naphtha crackers. FIG. 6 provides a schematic illustration of integration of an OCM system into a cracker facility. As shown in the simplified schematic of FIG. 2, a typical cracker unit, e.g., a naphtha cracker, includes the cracking furnace 204 and closely associated quenching systems 206. The $C_2+$ product gases from the cracker are then passed through appropriate treatment and compression systems 208 and 210, respectively, before routing to a coldbox and de-methanizer 212 to separate out any residual methane and hydrogen present in the cracker effluent. The $C_2+$ stream 218 is then routed through a separation or fractionation system that typically includes a de-ethanizer 222 for separating the $C_2$ components from the higher hydrocarbons, e.g., $C_3+$, an acetylene converter 224 that converts any acetylene produced during the cracking operation to ethylene, and a $C_2$ splitter 226 for separating the ethylene (stream 230) from the ethane (stream 232) in the product gas, which is recycled back into the cracking furnace 204.

In accordance with aspects of the present invention, an OCM reactor system is integrated into a more conventional cracker facility to provide a number of benefits, including feedstock flexibility, product slate selectability, and energy efficiency.

An exemplary illustration of this integration is schematically shown in FIG. 6. As shown, an OCM reactor system 402 again includes one, two, three or more OCM reactors, such as staged adiabatic reactors 404, 406 and 408, or one, two three or more serial or parallel isothermal reactors (not shown). In contrast to certain integrations within gas processing facilities, it will be appreciated that within a cracker process, the OCM reactor system may not share feedstock with the underlying facility. In particular, as noted above, the OCM reactor utilizes methane, and natural gas as its primary feedstock, e.g., in feed gas stream 602, while the cracker's feedstock (stream 202) will generally consist of ethane from NGLs, LPG, or naphtha. However, by providing an alternate source of ethylene, while relying upon many of the same unit operations for its production, an integrated OCM reactor system within a cracker facility provides significant advantages of feedstock flexibility. In particular, adverse fluctuations in feedstock price and/or availability of naphtha or ethane from NGLs can be partially, substantially, or completely mitigated through partial or substantial transition of a facility from a naphtha or ethane fed cracker facility to a methane fed OCM facility.

As shown, a methane containing feed gas 602 typically including an oxidant gas component, e.g., air or enriched air, is delivered to the OCM reactor system 402 and contacted with the OCM catalyst contained therein under OCM reaction conditions as described elsewhere herein. As shown, the OCM product gas 426, e.g., including ethylene, methane, ethane, and nitrogen, as well as other gases, such as CO and $CO_2$, is passed through a heat exchanger and compressor (not shown) before being passed into a cryogenic separation unit 606 (including, e.g., cryogenic separation units 120a and 120b in FIG. 1) for separation of nitrogen, CO and $CO_2$, and removal of at least some of the residual methane present in the OCM gas. The $C_2+$ rich stream from the separation unit (stream 608), containing ethylene, ethane, $C_3+$ hydrocarbons, as well as additional residual methane are then transferred to the downstream processing units of the cracker with which it is fluidly integrated, e.g., connected through a fluid coupling or connection. In particular, these product effluents from the cryogenic separation unit 606 may be routed into, e.g., cold-box 211 and de-methanizer 212 for separation of any residual methane, as well as any remaining hydrogen, CO and $CO_2$. For this integration, the methane rejection in the demethanizer portion of the cryogenic unit associated with the OCM reactor, e.g., de-methanizing cryogenic unit 120a, may preferably be tailored to be yield methane/$C_2+$ concentrations that are approximately equivalent to those concentrations for which the cracker demethanizer, e.g., demethanizer 212, is configured to address. As a result of reliance upon the cracker's existing demethanization capacity, the cryogenic separation unit associated with the OCM reactor, e.g., cryo unit 606, is deloaded, and may be provided with a correspondingly reduced capacity, yielding significant capital savings. As will be appreciated, a similar approach may be employed in the gas processing facility implementation described above. In particular, and with reference to FIG. 4, an additional demethanization operation may be included in stream 426, so as to be substantially equivalent to the methane content of the OCM output with the operating methane load of the facility's existing extraction unit, e.g., unit 120. In both the cracker and gas processing implementation, this results in a substantial reduction in capital expense, as it permits lower cost operations to integrate into the existing higher cost separations operations. As used herein, the term "substantially equivalent" in terms of methane concentration means that the methane concentration is within approximately 50% of the methane concentration normally or historically passed into the existing fractionation train of the gas facility or cracker facility, preferably within 20%, more preferably within about 10% of the normal or historical operating methane load.

The C2+ products are then routed into the cracker's fractionation train, e.g., de-ethanizer 222, acetylene reactor 224 and $C_2$ splitter 226, to recover ethylene and recycle ethane back into the cracker furnace 204.

In addition to providing feedstock flexibility to a cracker facility, an integrated OCM reactor system can also provide flexibility in selection of product slates, by allowing for a relaxation in the operating severity of the cracker process. In particular, the ratio of ethylene to co-products, e.g., propylene, etc., in a cracker process is a function of the cracking severity, which is a function of the reaction conditions. Because the highest demand is generally for ethylene, crackers tend to be operated to maximize ethylene production and minimize co-products, typically with an ethylene to propylene ratio of, e.g., greater than 2, using a naphtha feedstock. However, by supplementing ethylene production through the use of the integrated OCM reactor system, one can adjust the severity of the cracking process, e.g., to an ethylene to propylene ratio of less than 2, preferably less than or equal to about 1.5, less than or equal to 1.25, less than or equal to 1, or less, using the naphtha feedstock, to produce greater amounts of co-products as may be economically prudent given then current market conditions. Product slate optimization is particularly useful in a naphtha cracker environment where the co-product production is more meaningful than in an ethane cracking environment, where no significant co-products are produced.

In particularly preferred aspects, a cracker facility is supplemented using an integrated OCM reactor system in the amount of greater than about 5% of the ethylene produced on a weight for weight basis, greater than about 10% of the ethylene produced, on a weight for weight basis, preferably at least about 20%, more preferably at least about 30%, and in some cases greater than about 40% or even 50%. In particularly preferred aspects, at least 2% of the ethylene produced by the integrated facility is produced directly from the OCM reactor portion, preferably at least about 5%, more preferably at least about 10%, preferably at least about 20%, still more preferably at least about 30%, and in some cases at least about 40% or even 50% or greater.

In certain particularly preferred aspects, the contribution of the integrated OCM system, calculated on a weight for weight basis when including as ethylene produced from OCM as the total ethylene produced from the OCM reactor's feedstock (i.e., including both the ethylene produced directly from the OCM reaction, as well as ethylene from cracked ethane that is produced by the OCM reactors), is between about 10% and about 50%, more preferably between about 20% and about 50%, in certain preferred aspects, between about 30% and about 50%, and in still more preferred aspects, between about 40% and about 50%.

In a further embodiment, in order to provide even further product flexibility, the OCM effluent can be optionally routed into an ethylene oligomerization unit (either adiabatic or isothermal reactors described previously) that is designed to output a narrow band of aromatic hydrocarbons, e.g., BTX or BTEX, for a portion of the OCM output stream. In conjunction with the above described operational flexibility, this configuration would specifically provide the ability to change the severity of the cracking units in combination with the OCM unit and the optional ethylene oligomerization unit to output the desired mix of ethylene, propylene, C4 and C5 olefins, and provide additional flexibility on the selection of product slates of the overall system to produce greater amounts of high value aromatic compounds.

VII. Energy Integration

In addition to integration of the OCM reactor feeds and products into a conventional natural gas processing facility or its component units or systems, the present invention also provides for energy integration of the OCM process into existing natural gas processing systems. In particular, by exploiting the thermal energy produced in the highly exothermic OCM reaction, one can augment the thermal systems of an existing facility, e.g., heaters and boilers, to potentially reduce the overall energy that is needed to be separately generated for control of the other processing units in the facility.

As noted above, OCM is a highly exothermic reaction that, under preferred circumstances, operates at temperatures between about 400° C. and 950° C., depending upon the reactor process and system used, and in any event at reactor feed inlet temperatures of between about 400° C. and 600° C. Accordingly, initiation of the OCM reaction tends to require an initial input of thermal energy to elevate the reactants and catalysts to an appropriate reaction initiation, or "light off" temperature. Once initiated, the exothermic nature of the reaction typically produces sufficient thermal energy to maintain the reaction. Additionally, as the OCM catalytic process tends to generate a great deal of thermal energy, it can become necessary to remove a great deal of thermal energy from one or more of the reactor systems and/or the product gas streams, in order to efficiently manage the catalytic reaction and subsequent processing steps. In the context of the present invention, this excess of thermal energy may be used as one or both of a thermal and other energy source for other facility operations. As will be appreciated, in some configurations, overall reaction temperatures may span from light off temperatures of between 400° C. to 600° C., to maximum reactor temperatures of upwards of 950° C., depending upon whether the reactor system is operated in an isothermal or adiabatic configuration.

In one exemplary aspect, thermal energy created by the OCM reaction may be removed from OCM product gas streams, or in the case of isothermal reactor systems, other heat exchange media, to heat different components of the fractionation unit, e.g., the de-ethanizer, etc. Restated, rather than separately generating thermal energy to drive process aspects of a processing facility, the OCM reactor system provides some or all of that thermal energy. This provides an additional value add from the OCM reactor system, on top of the generation of highly valuable hydrocarbon products.

Figure 7:
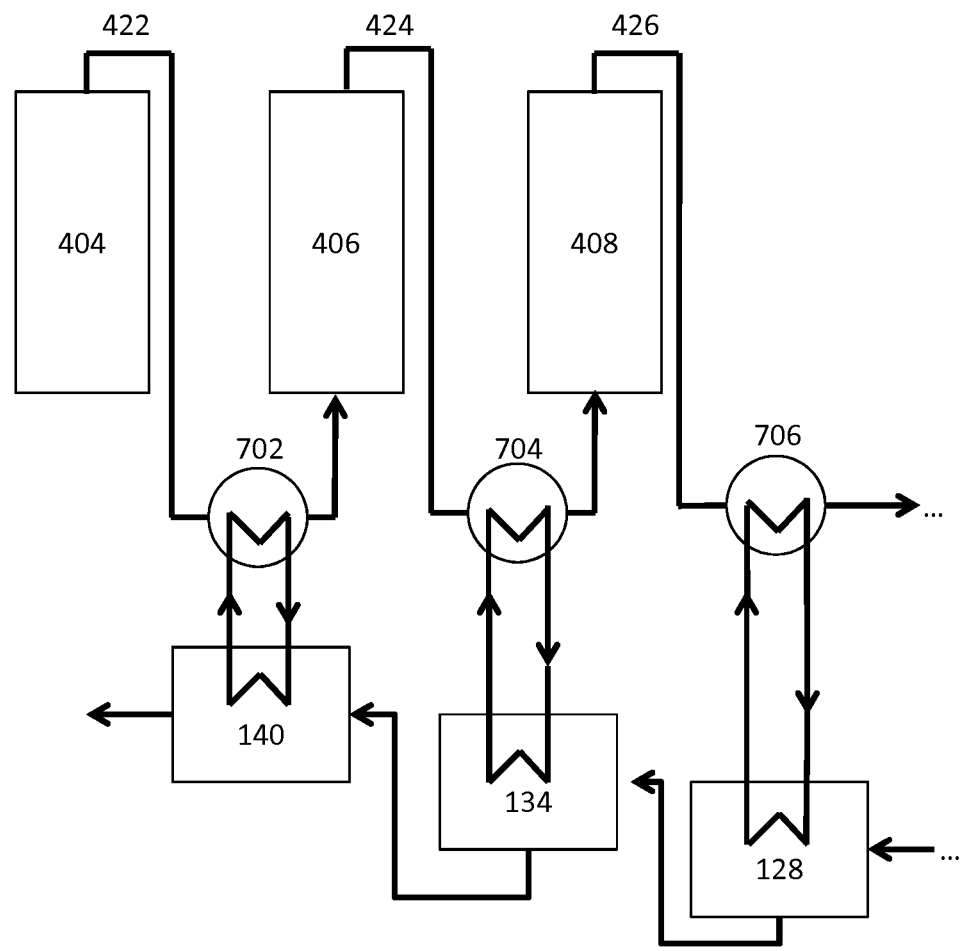
FIG. 7 provides a schematic illustration of integration of thermal energy systems from an OCM reactor system into thermal management processes for other processing systems within the exemplary natural gas processing facility.

In particular, with reference to the process illustrated in FIG. 7, OCM product gas streams, e.g., intermediate OCM product streams 422 and/or 424, and/or final OCM product stream 426, may be passed through one or more heat exchangers, e.g., heat exchangers 702 and 704, to reduce the temperature of the OCM product gas to temperatures appropriate for introduction into the subsequent reactors 406 and 408, respectively. Likewise, OCM product gas stream 426 may be passed through heat exchanger 706, to reduce the temperature of that stream to levels appropriate for the subsequent processing steps. Steam, water or any other heat exchange medium that is run through heat exchangers 702, 704 and/or 706 is routed through one or more of de-ethanizer 128, de-propanizer 134 and/or debutanizer 140, to provide thermal energy used in boiling off components in the fractionation process. This thermal energy may be used alone or to supplement the existing boiler capacity of a processing facility, and reduce the amount of energy required for that boiler capacity.

Additionally, thermal energy removed from the OCM reactor system or product streams may also be used to heat other process streams in the facility. For example, in addition to being used to heat the feed stream of the OCM reactor system to appropriate catalytic temperatures, the thermal energy from the OCM product streams or reactor systems may be used to heat cooled NGL streams following cryogenic extraction of those NGLs from the natural gas stream or the OCM reactor gas output. This is schematically illustrated in FIG. 7.

As will be appreciated, in using thermal transfer between the cooled NGL stream from the cryogenic extractor, one is simultaneously heating the NGL stream, while cooling the heat exchange medium that is used to cool the OCM product streams.

Alternatively, or additionally, thermal energy removed from the OCM system may be converted to electrical energy. For example, product gases, or in the case of isothermal reactors, a heat exchange medium that is carrying heat away from a reactor itself, may be passed through a heat exchanger to create steam which is used to drive the turbine of a electrical generator. The resulting electrical energy can then be used to augment the power used for operating additional systems of the facility, such as lighting, office systems, pumps, and other control systems. In such cases, the electrical generation system constitutes a processing unit, for the energy integration of the OCM reactors into the processing plant. In particular, thermal energy from the OCM reactor system is conveyed to the electrical generator to generate electricity from steam, which electrical energy is, in turn, conveyed to one or more different processing units within the plant, or to other operations within the plant, even back out to the electrical grid.

As noted above with respect to feed and product integration of OCM reactor systems in a gas processing facility or system, it will likewise be appreciated that in accordance with the invention, OCM reactor systems may have multipoint integration into a gas processing system in terms of feed, product, thermal energy and electrical energy, and may, in some cases be integrated as to most or all of the foregoing aspects. For example, OCM reactor feed may derive from the effluent of an extraction unit, while the product of the OCM reactor system may be fed to the extraction unit of the overall facility. Thermal energy derived from the exothermic OCM reactor system may concurrently be used to augment boiler capacity used to operate the fractionation systems and or heat the feed gases used in the OCM reactor system. Further, excess steam generation from the exothermic OCM reactor system may concurrently be used in electricity generation using a conventional steam electric generator system. As will be appreciated, any combination of multi-point integration may be practiced in accordance with the invention.

As with the NGL processing facilities described above, energy conservation and re-use is also applicable to cracker facilities for the purposes of "on-purpose" steam generation, e.g., for driving turbines, boilers, compressors, etc. In particular, heat generated by the OCM reactor systems may be used to supplement or supplant the boilers typically used in cracker operations. Likewise, cooled streams or heat exchange media, may be circulated through heat exchangers in the OCM reactor system, to cool effluents from that system. Further, heat energy may again be converted to electrical energy, as described above.

In some additional aspects, the integrated systems of the invention may be used in the generation and collection of carbon dioxide for use in still other natural gas processes. In particular, bulk carbon dioxide has found recycle uses in the oil and gas industry in, for example, enhanced oil recovery ("EOR") processes. In EOR processes, CO2 is injected into oil reservoirs to displace oil from porous rock, as well as provide reduced viscosity.

In the context of the systems described herein, CO2 generated as a by-product in an OCM reaction, is separated in an extraction process. Rather then being discarded, however, the CO2 is instead collected for use. The collected CO2 may be stored on-site at the facility or it may be transported to a site where it will be used, such as an oil filed. Such transportation may involve truck, train or pipeline transport, depending upon the amount of $CO_2$ involved. In addition to using a 'waste' product from the overall system for a useful end, the beneficial use of $CO_2$ can also provide gas facility operators with carbon credits for sale or trade with other producers of greenhouse gases. These credits provide additional value to facility operators from the integrated OCM systems described herein.

Although described in some detail for purposes of illustration, it will be readily appreciated that a number of variations known or appreciated by those of skill in the art may be practiced within the scope of present invention. All terms used herein are intended to have their ordinary meaning unless an alternative definition is expressly provided or is clear from the context used therein. For methods recited herein, to the extent that a composition of the invention is disclosed as being provided in a method step, it will be appreciated that disclosure of such provision implicitly discloses the preparation of such composition in a transformative fashion. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

The invention claimed is:

1. A natural gas processing system, comprising:
   (a) an oxidative coupling of methane (OCM) reactor system comprising at least one reactor vessel having at least one OCM catalyst disposed therein and configured to operate with an inlet temperature between about 400° C. and about 600° C. to yield a product stream comprising at least two different hydrocarbon compounds, wherein the OCM catalyst comprises a nanostructured component which comprises a nanowire component having an aspect ratio greater than ten;
   (b) one or more of (i) an extraction system for separating at least one hydrocarbon compound from at least one non-hydrocarbon compound as part of the product stream or a feed stream to the at least one reactor vessel, and (ii) a fractionation system for separating the at least two different hydrocarbon compounds; and
   (c) an interconnected pipeline, the interconnected pipeline fluidly connecting (i) an inlet of the OCM reactor system to an outlet of the extraction system and/or the fractionation system, or (ii) an outlet of the OCM reactor system to an inlet of the extraction system and/or the fractionation system.

2. The processing system of claim 1, wherein the extraction system comprises a methane rich effluent outlet, and wherein the inlet of the OCM reactor system is fluidly coupled to the methane rich effluent outlet of the extraction system, to convey methane rich effluent from the extraction system to the reactor vessel.

3. The processing system of claim 1, wherein the fractionation system comprises one or more of a de-ethanizing unit, a de-propanizing unit and a de-butanizing unit, and the outlet of the OCM reactor system is fluidly coupled to an inlet of the fractionation system for transferring an OCM product in the product stream to the fractionation system.

4. The processing system of claim 3, wherein the outlet of the OCM reactor system is fluidly coupled to an inlet of the de-ethanizing unit in the fractionation system for transferring an OCM product to the de-ethanizing unit.

5. The processing system of claim 1, wherein the outlet of the OCM reactor system is fluidly coupled to the inlet of the extraction system for transferring an OCM product to the extraction system.

6. The processing system of claim 2 or 5, wherein the extraction system is selected from a cryogenic extraction system and a lean oil extraction system.

7. The processing system of claim 2 or 5, wherein the extraction system comprises a cryogenic extraction system, wherein the cryogenic extraction system comprises a nitrogen rejection unit and a cryogenic de-methanizing unit for separating methane from the OCM product.

8. The processing system of claim 1, wherein the at least one OCM catalyst catalyzes an OCM reaction of methane and oxygen at a reactor inlet temperature of between about 400° C. and 600° C., and a pressure of less than 150 psig, wherein the reaction has methane conversion of at least 10% in a single process pass and a C2+selectivity of at least 50%.

9. The processing system of claim 1, wherein the nanowire component comprises a catalytic nanowire component.

10. The processing system of claim 1, wherein the inlet of the OCM reactor system is fluidly coupled to an outlet of a purification system, an outlet of the extraction system or an outlet of the fractionation system, and the outlet of the OCM reactor system is fluidly connected to an inlet of one or more of the extraction system and the fractionation system.

11. A natural gas processing system, comprising:
(a) an oxidative coupling of methane (OCM) reactor system comprising at least one reactor vessel having an OCM catalyst disposed therein and configured to operate with an inlet temperature between about 400° C. and about 600° C. to yield a product stream comprising at least two different hydrocarbon compounds, wherein the OCM catalyst comprises a nanostructured component which comprises a nanowire component having an aspect ratio greater than ten;
(b) an extraction system for separating at least one non-hydrocarbon compound from at least one hydrocarbon compound as part of the product stream or a feed stream to the at least one reactor vessel;
(c) a fractionation system for separating the at least two different hydrocarbon compounds; and
(d) an interconnected pipeline fluidly connecting (i) an inlet of the OCM reactor system to an outlet of the fractionation system and/or the extraction system, or (ii) an outlet of the OCM reactor system to an inlet of the extraction system and/or the fractionation system.

12. The processing system of claim 11, wherein the extraction system comprises a methane rich effluent outlet, and wherein the inlet of the OCM reactor system is fluidly coupled to the methane rich effluent outlet of the extraction system, to convey methane rich effluent from the extraction system to the at least one reactor vessel.

13. The processing system of claim 11, wherein the fractionation system comprises one or more of a de-ethanizing unit, a de-propanizing unit and a de-butanizing unit, and the outlet of the OCM reactor system is fluidly coupled to an inlet of the fractionation system for transferring an OCM product in the product stream to the fractionation system.

14. The processing system of claim 13, wherein the outlet of the OCM reactor system is fluidly coupled to an inlet of the de-ethanizing unit in the fractionation system for transferring an OCM product to the de-ethanizing unit.

15. The processing system of claim 11, wherein the outlet of the OCM reactor system is fluidly coupled to the inlet of the extraction system for transferring an OCM product to the extraction system.

16. The processing system of claim 11, wherein the extraction system is selected from a cryogenic extraction system and a lean oil extraction system.

17. The processing system of claim 11, wherein the extraction system comprises a cryogenic extraction system, wherein the cryogenic extraction system comprises a nitrogen rejection unit and a cryogenic de-methanizing unit for separating methane from the OCM product.

18. The processing system of claim 11, wherein the OCM catalyst catalyzes an OCM reaction of methane and oxygen at a reactor inlet temperature of between about 400° C. and 600° C., and a pressure of less than 150 psig, wherein the reaction has methane conversion of at least 10% in a single process pass and a C2+selectivity of at least 50%.

19. The processing system of claim 11, wherein the nanowire component comprises a catalytic nanowire component.

20. The processing system of claim 11, wherein the inlet of the OCM reactor system is fluidly coupled to an outlet of a purification system, an outlet of the extraction system or an outlet of the fractionation system, and the outlet of the OCM reactor system is fluidly connected to an inlet of one or more of the extraction system and the fractionation system.

* * * * *